(12) United States Patent
Choi

(10) Patent No.: US 11,795,139 B2
(45) Date of Patent: Oct. 24, 2023

(54) PHENYLCARBAMATE CRYSTALLINE FORM AND METHOD FOR MANUFACTURING THE SAME

(71) Applicant: BIO-PHARM SOLUTIONS CO., LTD., Suwon-si (KR)

(72) Inventor: Yong Moon Choi, Irvine, CA (US)

(73) Assignee: BIO-PHARM SOLUTIONS CO., LTD., Suwon-si (KR)

( * ) Notice: Subject to any disclaimer, the term of this patent is extended or adjusted under 35 U.S.C. 154(b) by 140 days.

(21) Appl. No.: 17/837,929

(22) Filed: Jun. 10, 2022

(65) Prior Publication Data

US 2023/0101131 A1    Mar. 30, 2023

(30) Foreign Application Priority Data

Aug. 5, 2021 (KR) .......... 10-2021-0103371

(51) Int. Cl.
*C07C 271/16* (2006.01)
(52) U.S. Cl.
CPC ........ *C07C 271/16* (2013.01); *C07B 2200/13* (2013.01)
(58) Field of Classification Search
CPC .......... C07C 271/16; C07B 2200/13
USPC ........................................ 560/160
See application file for complete search history.

(56) References Cited

U.S. PATENT DOCUMENTS

2008/0085930 A1   4/2008  Peterson
2013/0165408 A1   6/2013  Choi

FOREIGN PATENT DOCUMENTS

| KR | 10-2009-0076958 A | 7/2009 |
| KR | 10-2014-0108226 A | 9/2014 |
| KR | 10-2014-0113918 A | 9/2014 |
| KR | 10-2014-0113919 A | 9/2014 |

OTHER PUBLICATIONS

Decision to Grant issued on Korean Patent Application No. KR 10-2021-0103371 dated Apr. 21, 2022, 3 pages.

*Primary Examiner* — Ana Z Muresan
(74) *Attorney, Agent, or Firm* — ROTHWELL, FIGG, ERNST & MANBECK, P.C.

(57) ABSTRACT

The present invention relates to a crystalline form of a phenyl carbamate derivative compound and a use thereof, and more particularly, to a more thermodynamically stable crystal, i.e., a Pattern 1 crystalline form, and a preparation method thereof. Amorphous and crystalline forms were prepared using various solvents, and among these, a thermodynamically stable Pattern 1 crystalline form and a pharmaceutical use of this crystalline form are provided.

5 Claims, 22 Drawing Sheets

PHENYLCARBAMATE CRYSTALLINE FORM AND METHOD FOR MANUFACTURING THE SAME

TECHNICAL FIELD

This application claims priority based on Korean Patent Application No. 10-2021-0103371 filed on Aug. 5, 2021, the disclosures of which are incorporated herein by reference in their entirety.

The present invention relates to a crystalline form of a phenyl carbamate compound, a method of preparing the same and a pharmaceutical composition including the same.

BACKGROUND ART

Phenyl carbamate compounds are compounds known to have an effect on various neurological disorders including multiple sclerosis, Lou Gehrig's disease, epilepsy and central nervous system disorders, muscle diseases, stroke, psychiatric disorder and memory loss-related diseases. These compounds have excellent pharmacological effects on various diseases due to its high pharmacological activity, and have been developed and widely used as medicines due to low toxicity.

Among the phenyl carbamate compounds, (1-(2-chlorophenyl)-(S)-1-hydroxypropyl-(S)-2-carbamate (JBPOS0101) is a material that is verified to be particularly effective in treatment or prevention of multiple sclerosis (Korean Patent No. 10-2014-0113919 A) or Lou Gehrig's disease (10-2014-0113918 A), and research is being attempted to synthesize various crystalline forms of the material such that they have more improved stability and can be used in various formulations.

DISCLOSURE

Technical Problem

According to the research on the material, the inventors conducted research to improve the stability of a material related to thermodynamic stability, in which a carbamate group is shifted to an adjacent hydroxyl group particularly under a basic aqueous condition, among phenyl carbamate compounds, and thus the present invention for a crystalline material which is thermodynamically stable and has excellent solid characteristics was completed.

Therefore, the present invention is directed to providing a crystalline form of a phenyl carbamate derivative compound, 1-(2-chlorophenyl)-(S)-1-hydroxypropyl-(S)-2-carbamate (JBPOS0101), which is thermodynamically stable and anhydrous and exhibits excellent solid characteristics.

The present invention is also directed to providing a pharmaceutical composition including the crystalline form of 1-(2-chlorophenyl)-(S)-1-hydroxypropyl-(S)-2-carbamate (JBPOS0101).

The present invention provides a crystalline form of 1-(2-chlorophenyl)-(S)-1-hydroxypropyl-(S)-2-carbamate (JBPOS0101), represented by Formula 1 below.

[Formula 1]

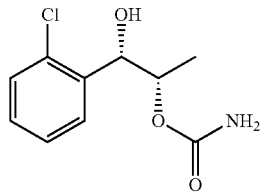

The present invention also provides a pharmaceutical composition including the crystalline form of 1-(2-chlorophenyl)-(S)-1-hydroxypropyl-(S)-2-carbamate (JBPOS0101).

Hereinafter, the present invention will be described in detail.

The term "crystalline form" used herein refers to a crystalline solid that does not include a solvent molecule in a substantially fixed molar ratio in a crystal lattice, that is, a crystalline solid, not a solvate.

To prepare the crystalline form of (1-(2-chlorophenyl)-(S)-1-hydroxypropyl-(S)-2-carbamate), the API polymorphism of amorphous (1-(2-chlorophenyl)-(S)-1-hydroxypropyl-(S)-2-carbamate (JBPOS0101/S-P-17001, Bio-Pharm Solutions Co. Ltd.) was screened, and various forms of polymorphic patterns were obtained by screening with various solvents. Among these patterns, an anhydrous crystalline form, Pattern 1 (ED01748-006-001-00), which is thermodynamically stable at both room temperature and a high temperature (50° C.), was completed.

The Pattern 1 crystalline form has a melting point of 89° C., and has no considerable mass loss in TGA until decomposed at about 200° C. or more. During a GVS experiment, it was confirmed that there is almost no mass increase within a 0-90% RH range (0.14%), and after the GVS experiment, it was confirmed by XRPD that even when exposed to a high humidity at 40° C./75% RH or RT/97% RH, the Pattern 1 crystalline form has no morphological change.

The pattern I crystalline form of (1-(2-chlorophenyl)-(S)-1-hydroxypropyl-(S)-2-carbamate) has peaks at diffraction angles (2θ) of 17/b 6.662°, 8.153°, 9.801°, 11.303°, 11.660°, 13.280°, 13.435°, 14.703°, 16.243°, 16.948°, 19.091°, 19.419°, 20.443°, 21.124°, 24.202°, 24.619°, 28.998° and 31.697° in X-ray powder diffraction (XRPD) patterns. Additional peaks may also be shown at one or more diffraction angles (2θ) of 7.392°, 12.068°, 12.874°, 13.913°, 15.256°, 17.796°, 18.266°, 18.572°, 19.895°, 22.076°, 22.354°, 22.673°, 23.174°, 23.582°, 25.260°, 25.435°, 25.932°, 26.138°, 26.614°, 26.983°, 27.965°, 28.256°, 28.805°, 29.319°, 29.690°, 30.247°, 30.483°, 32.668° and 33.414°.

In one embodiment of the present invention, the crystalline form of (1-(2-chlorophenyl)-(S)-1-hydroxypropyl-(S)-2-carbamate) was dissolved in one or more solvents selected from 1,4-dioxane, t-butanol, dichloromethane and/or water, or maintained for a predetermined time after dissolution, thereby obtaining an amorphous product. Afterward, the resulting product was crystallized by polymorphic screening using a solvent, thereby obtaining polymorphic patterns.

As a solvent used in the polymorphic screening, a solvent selected from the group consisting of diethyl ether, pentane, ethyl formate, tert-butylmethyl ether, acetone, methyl acetate, chloroform, methanol, tetrahydrofuran, diisopropyl ether, ethyl acetate, ethanol, methyl ethyl ketone, acetonitrile, 2-propanol, tert-butanol, 1,2-dimethoxyethane, isopropyl acetate, 1-propanol, 2-butanol, heptane, water, formic acid, 1,4-dioxane, propyl acetate, 2-pentanone, 2-methyl-1-propanol, toluene, isobutyl acetate, methyl isobutyl ketone, 1-butanol, acetic acid, 2-methoxyethanol, butyl acetate, methyl butyl ketone, 3-methyl-1-butanol, 2-ethoxyethanol, 1-pentanol, cumene, anisole, benzonitrile, dimethyl sulfoxide and benzyl alcohol, and a mixed solvent thereof was used, and more preferably, a solvent for screening the Pattern 1 crystalline form, such as a solvent selected from the group consisting of acetone, chloroform, MeOH, tetrahydrofuran, diisopropyl ether, ethanol (EtOH), methyl ethyl ketone, acetonitrile, 2-propanol, tert-butanol), 1,2-dimethoxyethane (DME), 1-propanol, 2-butanol, water, 1,4-dioxane, 2-methyl-1-propanol, 2-methoxyethanol, butyl acetate, methyl butyl ketone, 3-methyl-1-butanol, 1-pentanol, cumene and anisole, and a mixed solvent thereof was used.

In another aspect of the present invention, the present invention provides a pharmaceutical composition including the crystalline form of 1-(2-chlorophenyl)-(S)-1-hydroxypropyl-(S)-2-carbamate (JBPOS0101).

The pharmaceutical composition may be used as a pharmaceutical composition for a similar use to that of phenyl carbamate or a derivative thereof, and more specifically, a composition for treating or preventing one or more diseases selected from the group consisting of muscle relaxation, spasticity, spasms, central nervous system disorders, Lou Gehrig's disease, multiple sclerosis, chronic pain, stroke, epilepsy, epilepsy-related syndrome, pediatric epilepsy, pediatric epilepsy-related syndrome, memory loss-related disease, nerve gas-induced disease, psychiatric disorder, movement disorder and neurological injury disease.

More specifically, wherein the memory loss-related disease comprising senile dementia or Alzheimer's disease; wherein the nerve gas-induced disease comprising spasm, gastrointestinal distress, emesis, rhinorrhea, miosis, bronchoconstriction, fasciculation, floppy paralysis, apnea, diaphoresis and diarrhea; wherein the psychiatric disorder comprising depression, bipolar disorders, anxiety disorder and seizures; wherein the movement disorder comprising ataxia, corticobasal ganglionic degeneration (CBGD), dyskinesia, dystonia, tremors, essential tremor, Parkinsonian tremor, hereditary spastic paraplegia, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), hemibalismus, hemi-facial spasm, Wilson's disease, stiff man syndrome, akinetic mutism, psychomotor retardation, painful legs moving toes syndrome, a gait disorder, and a drug-induced movement disorder; wherein the neurological injury disease comprising neurodegenerative disease, autism spectrum disease and prion diseases; wherein the neurodegenerative disease is selected from the group consisting of Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia; wherein the autism spectrum disease is selected from the group consisting of autism, Asperger syndrome and pervasive developmental disorder not otherwise specified (PDD-NOS); and wherein the prion diseases is selected from the group consisting of Creutzfeldt-Jakob disease, Gerstmann-Straussler-Scheinker disease, Kuru disease and fatal familial insomnia.

In addition, the pharmaceutical composition of the present invention may be formulated in various oral dosage forms or parenteral dosage forms. For example, the pharmaceutical composition may be prepared in any formulation for oral administration such as tablets, pills, soft/hard capsules, liquids, suspensions, emulsions, syrups, granules, and elixirs. The oral formulation may include a pharmaceutically available carrier such as a diluent such as lactose, dextrose, sucrose, mannitol, sorbitol, cellulose and/or glycine, or a glidant such as silica, talc, stearic acid and a magnesium or calcium salt thereof and/or polyethylene glycol, in addition to the active ingredient, according to a conventional composition of each formulation.

In addition, when the oral formulation is a tablet, it may include a binder such as magnesium aluminum silicate, starch paste, gelatin, tragacanth, methyl cellulose, sodium carboxymethylcellulose and/or polyvinylpyrrolidine, and in some cases, it may also include a disintegrant such as starch, agar, alginic acid or a sodium salt thereof or a boiling mixture, and/or an absorbent, a colorant, a flavoring agent or a sweetening agent.

In addition, the pharmaceutical composition may be formulated in a parenteral dosage form, and administered by a parenteral administration method such as subcutaneous injection, intravenous injection, intramuscular injection or intrathoracic injection. Here, to prepare the parenteral formulations, the pharmaceutical composition may be prepared in a solution or suspension by mixing an active ingredient with a stabilizing agent or buffer in water, and the solution or suspension may be dispensed into a unit dosage form of an ampoule or vial.

In addition, the pharmaceutical composition may be sterilized or further include additives such as a preservative, a stabilizing agent, a wetting agent or emulsifier, a salt for osmotic control and/or a buffer, and may further include other therapeutically useful materials. The pharmaceutical composition may be prepared by a conventional method such as mixing, granulation or coating.

In addition, the active ingredient may be administered daily at a therapeutically effective amount of 0.01 to 750 mg/kg (body weight), and preferably 0.1 to 500 mg/kg (body weight) for mammals including humans. The term "therapeutically effective amount" means an amount that can exhibit a relieving and/or therapeutic effect of the disease. Such a pharmaceutical composition may be administered once or in a two or more divided portions a day via oral or parenteral routes.

Advantageous Effects

The present invention relates to an anhydrous Pattern 1 crystalline form, which has a higher melting point and is thermodynamically stable with almost no mass loss until decomposition, compared to other salts or crystalline forms of 1-(2-chlorophenyl)-(S)-1-hydroxypropyl-(S)-2-carbamate (JBPOS0101), and has excellent storage stability because there is no morphological change confirmed by XRPD even when exposed to humidity.

MODES OF THE INVENTION

Figure 1:
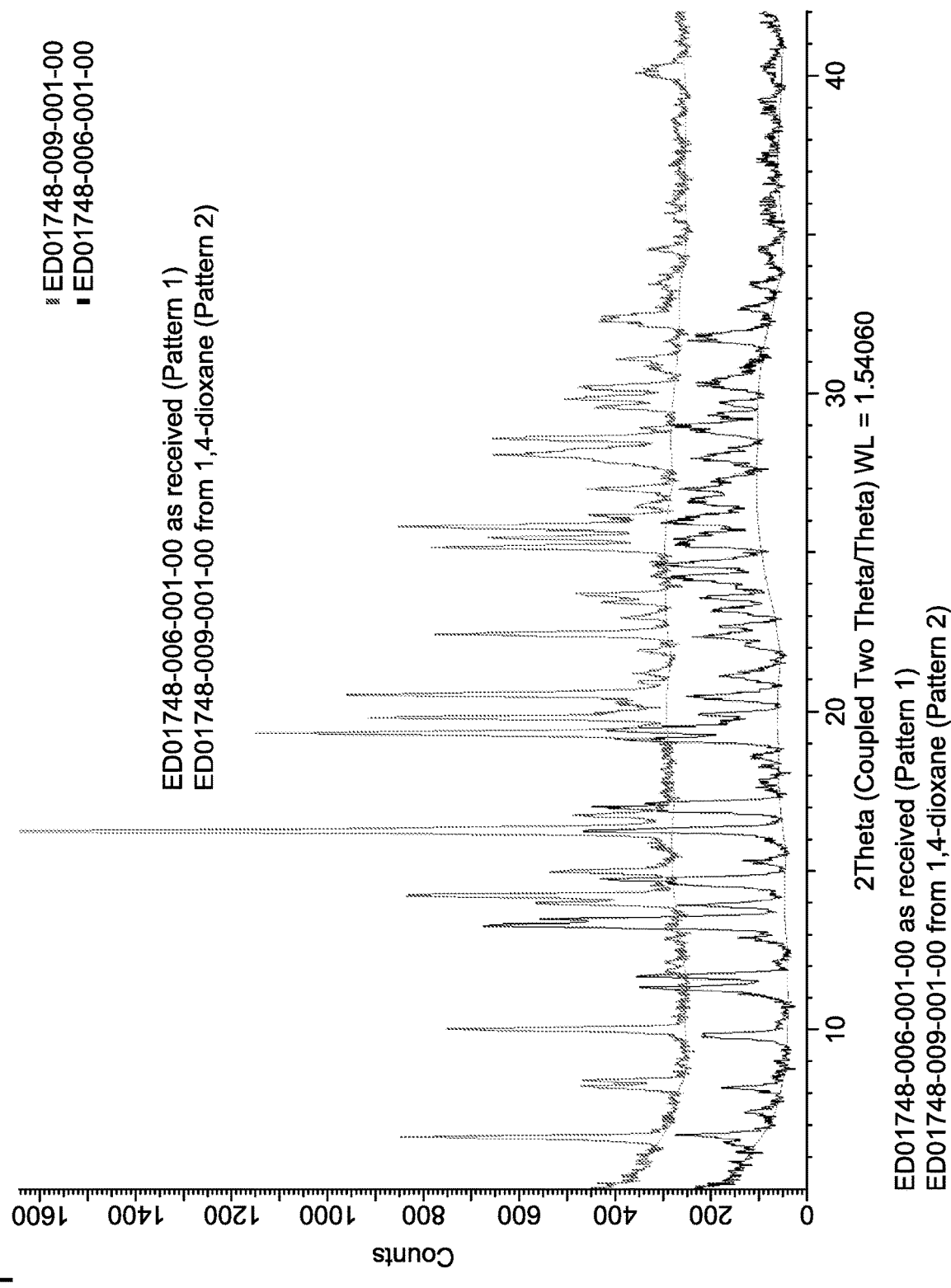
FIG. 1 shows the result of comparing XRPD patterns after 1,4-dioxane treatment (ED01748-009-001-00, Pattern 2) to form amorphous 1-(2-chlorophenyl)-(S)-1-hydroxypropyl-(S)-2-carbamate (JBPOS0101).

Hereinafter, the present invention will be described in detail with reference to examples to help in understanding the present invention. However, examples according to the present invention may be modified into a variety of different forms, and it should not be construed that the scope of the present invention is limited to the following examples. The examples of the present invention are provided to more completely explain the present invention to those of ordinary skill in the art.

<Experimental Methods>

1. X-Ray Powder Diffraction (XRPD)

XRPD patterns were detected by CuKα irradiation (30 kV, 10 mA) using a Bruker AXS D2 diffractometer. The analysis was performed using 0-0 geometry and a LynxEye detector at 5 to 42° 2θ with a step size of 0.024° 2θ at 0.1 sec/step.

The software used for data collection was DIFFRAC.SUITE, and the data was analyzed and presented using Diffrac Plus EVA v 16.0.0.0.

Samples were run at ambient conditions and prepared as flat specimens using powder received without grinding. About 1 to 2 mg of the sample was lightly pressed on a silicon wafer to obtain a flat surface.

2. Single Crystal X-Ray Diffraction (SCXRD)

SCXRD analysis was performed by Rbar3 Ltd.

3. Nuclear Magnetic Resonance Spectroscopy (NMR)

A solution phase $^1$H NMR spectrum was obtained using a 5-mm PABBO probe-installed Bruker AVIIIHD NMR spectrometer operated at 400.1326 MHz. Samples were prepared with d6-DMSO unless otherwise specified and referenced using TMS internal standards.

4. Differential Scanning Calorimetry (DSC)

DSC data was collected on a Mettler DSC 3+ equipped with a 34 position auto-sampler. The instrument was calibrated for energy and temperature using certified indium. Generally, 0.5 to 3 mg of each sample was heated from 30 to 300° C. at 10° C./min in a pinhole aluminum pan. A nitrogen purge was maintained over the sample at 50 mL/min STARe v15.00 was used for instrument control and data processing.

5. Thermogravimetric Analysis (TGA)

TGA data were collected on a Mettler TGA 2 equipped with a 34 position auto-sampler. The instrument was calibrated for energy and temperature using certified isotherm and nickel. Generally, 0.5 to 30 mg of each sample was heated at from 30 to 400° C. at 10° C./min in a pinhole aluminum pan. A nitrogen purge was maintained over the sample at 50 mL/min. STARe v15.00 was used for instrument control and data processing.

6. Polarized Light Microscopy (PLM)

A digital video camera-equipped Nikon DLM polarization microscope was used to capture sample images. A small amount of sample was placed on a glass slide, mounted in an immersion oil, and covered with a glass slip for individually isolating particles as much as possible. The sample was observed with appropriate magnification and partial polarization, coupled to a 2 additive color filter.

7. Particle Size Distribution (PSD) by Laser Diffraction

PSD was measured using a Sympatec HELOS/BF particle sizer equipped with a RODOS/ASPIROS dry dispenser operating at 2.5 Bar with a sled speed of 25 mm/s. R1 0.1/0.18 μm-35 μm and R3 0.5/0.9 μm-175 μm lenses were combined and used for observation. Unless specified otherwise, a trigger condition of 1 ms 0.2% Ch27 was used.

8. Gravimetric Vapor Sorption (GVS)

Sorption isotherms were obtained using an SMS DVS intrinsic water absorption analyzer controlled by SMS Analysis Suite software. A sample temperature was maintained at 25° C. throughout. Humidity was controlled by a mixed stream of dry and wet nitrogen with a total flow rate of 200 mL/min. The relative humidity was measured with a calibrated Rotronic probe (dynamic range: 1.0-100% RH) located near the sample. The weight change (mass relaxation) of the sample as a function of % RH was continuously monitored using a microbalance (accuracy ±0.005 mg). 5 to 20 mg of the sample was stored in a prepared stainless steel mesh basket under atmospheric conditions.

9. Measurement of Thermodynamic Solubility by UPLC

A thermodynamic solubility in water was determined by providing a suitable concentration of compound prepared by suspending a sufficient compound in water or buffer according to estimated solubilities of the medium and the compound. Quantification was done by UPLC with reference to a standard calibration curve. A solubility was calculated with QuanLynx using a peak area determined by the integration of a peak found at the same retention time as the main peak in the standard injection.

<Example 1> Preparation of Amorphous 1-(2-chlorophenyl)-(S)-1-hydroxypropyl-(S)-2-carbamate 1-(2-chlorophenyl)-(S)-1-hydroxypropyl-(S)-2-carbamate (JBPOS0101/S-P-17001) was obtained from Bio-Pharm Solutions Co. Ltd. A method of preparing a phenyl carbamate compound, JBPOS0101, is described in Korean Patent No. 10-2014-0113918 A.

The CRL batch reference number for a crystalline form of 1-(2-chlorophenyl)-(S)-1-hydroxypropyl-(S)-2-carbamate is ED01748-006-001-00, and has characteristics of Table 1 below.

For screening of various polymorphisms of the material, first, the material was amorphized, and the resulting amorphous material was used as a material for polymorphic screening with various solvents.

<1-1> Preparation of Amorphous Form by 1,4-dioxane

Figure 2:
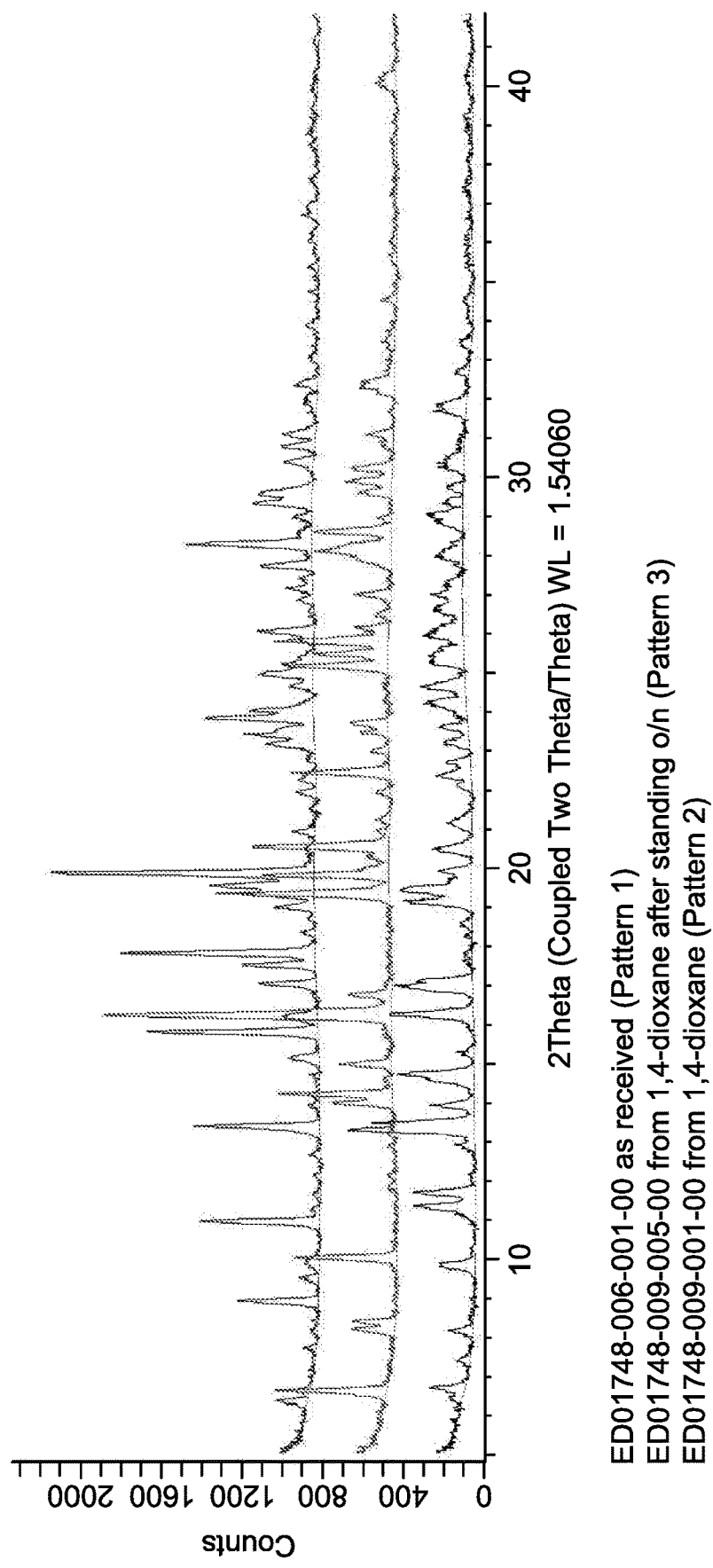
FIG. 2 shows the result of comparing XRPD patterns after 1,4-dioxane treatment (ED01748-009-001-00, Pattern 2) and storing overnight (ED01748-009-005-00, Pattern 3) to form amorphous 1-(2-chlorophenyl)-(S)-1-hydroxypropyl-(S)-2-carbamate (JBPOS0101).

A portion of ED01748-006-001-00 (15 mg) was dissolved in 1,4-dioxane (0.1 mL). A white solid ED01748-009-001-00 was prepared by flash freezing in a dry ice/acetone bath and freeze-drying the prepared solution, and as a result of XRPD analysis, a crystalline form (Pattern 2) with a different pattern was identified (FIG. 1). In addition, as a result of reanalysis of the ED01748-006-001-00 sample after being left overnight on the XRPD disc under laboratory conditions, a crystalline form with a novel pattern (ED01748-009-005-00, Pattern 3) was identified (FIG. 2).

<1-2> Preparation of Amorphous Form by 1,4-Dioxane/Water

ED01748-006-001-00 (10 mg) was dissolved in 1,4-dioxane (0.2 mL) and water (0.1 mL).

A white solid ED01748-013-001-00 was prepared by flash freezing in a dry ice/acetone bath and freeze-drying the prepared solution. As a result of XRPD analysis of the solution, a crystalline form with the same pattern as obtained by freeze-drying in 1,4-dioxane (Pattern 2) was identified.

<1-3> Preparation of Amorphous Form by t-Butanol

Figure 3:
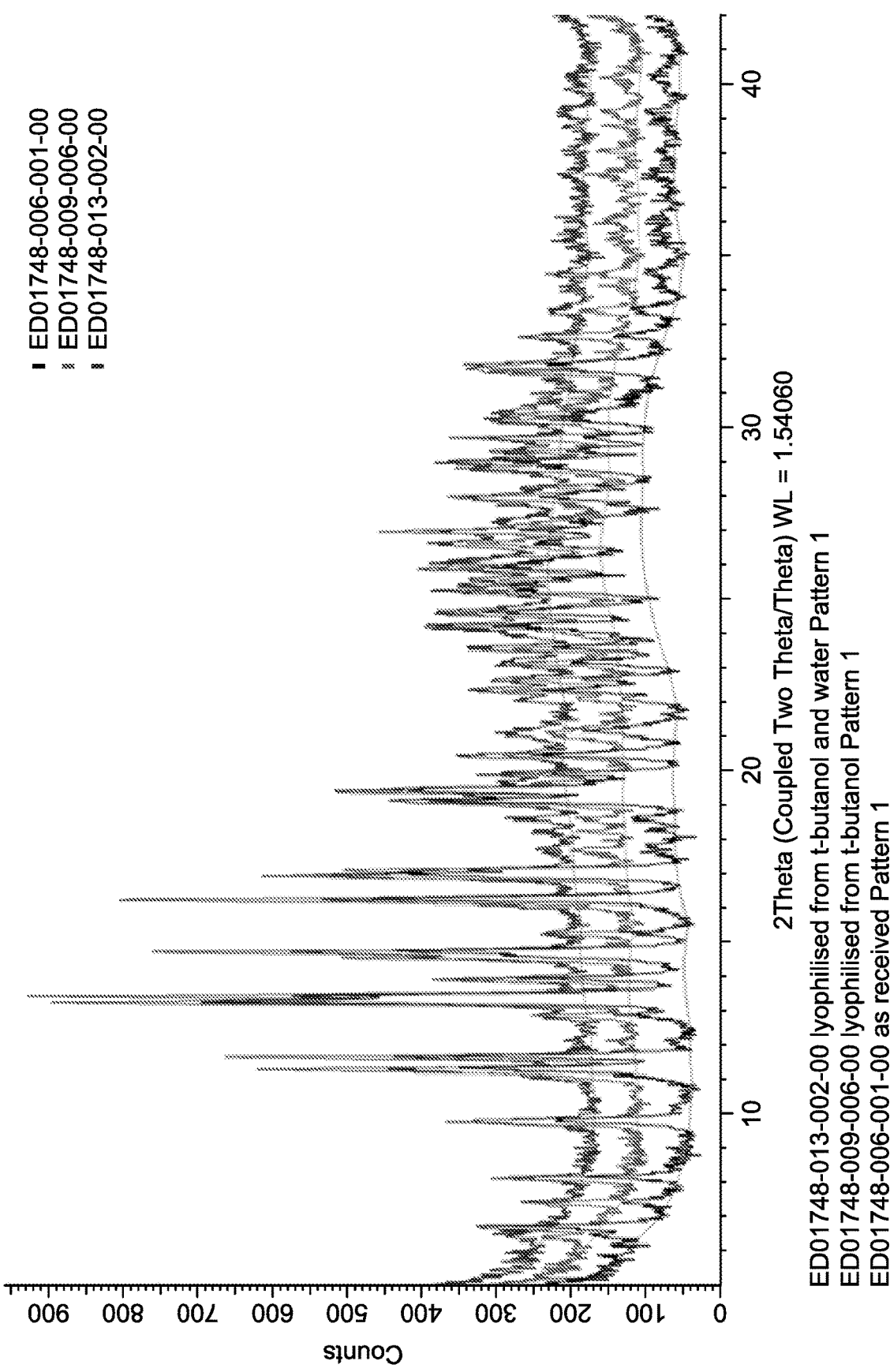
FIG. 3 shows the result of comparing XRPD patterns after t-butanol treatment (ED01748-009-006-00, Pattern 1), treatment of t-butanol with water (ED01748-013-002-00, Pattern 1) to form amorphous 1-(2-chlorophenyl)-(S)-1-hydroxypropyl-(S)-2-carbamate (JBPOS0101).

A portion of ED01748-006-001-00 (10 mg) was dissolved in t-butanol (0.25 mL). ED01748-009-006-00 with high viscosity was obtained by flash freezing in a dry ice/acetone bath and freeze-drying the prepared solution. According to the XRPD analysis of the material, the crystallinity of Pattern 1 was identified (FIG. 3).

TABLE 1

| | | | |
|---|---|---|---|
| Bio-Pharm Solutions Co. Ltd. Batch reference | JBPOS0101/S-P-17001 | | |
| CRL batch reference | ED01748-006-001-00 | | |
| Appearance | White crystalline solid | | |
| Molecular formula | $C_{10}H_{12}ClNO_3$ | | |
| Molecular weight | 229.66 | | |
| $^1$H NMR | Consistent with structure | | |
| UPLC Purity[3] | 98.6% | | |
| XRPD | Crystalline by XRPD, assigned as Pattern 1 | | |
| DSC | DSC shows a very small endothermic event of onset 81° C. (peak 82° C.), followed by a sharp endothermic event of onset 89° C. (peak 90° C.) consistent with a melt. Broad peak of onset 229° C. - decomposition | | |
| TGA | TGA shows 95% of mass remaining at 237° C. with no significant mass loss until above ca. 200° C. 100% of mass was lost by 305° C. | | |
| PSD | D10 | D50 | D90 |
| | 0.95 μm | 4.51 μm | 41.92 μm |
| Log D (shake flask at pH 5), Log P | Log $D_{pH5}$ = 1.32, Log P = 1.32 | | |
| GVS | Shows a 0.14% mass increase over the second sorption cycle (0-90% RH) | | |
| XRPD post GVS (ED01748-006-002-00) | Shows no change in form by XRPD post GVS | | |
| XRPD post storage at 40°C/75% RH for 7 days (ED01748-006-003-00) | Shows no change in form by XRPD post storage at 40°C/75% RH for 7 days | | |
| UPLC purity post storage at 40°C/75% RH for 7days (ED01748-006-003-00) | 97.4% | | |
| $^1$H NMR post storage at 40°C/75% RH for 7 days (ED01748-006-003-00) | Consistent with structure | | |
| XRPD post storage at RT/97% RH for 7 days (ED01748-006-004-00) | Shows no change in form by XRPD post storage at RT/97% RH for 7 days | | |
| UPLC purity post storage at RT/97% RH for 7 days (ED01748-006-004-00) | 97.7% | | |
| $^1$H NMR purity post storage at RT/97% RH for 7 days (ED01748-006-004-00) | Consistent with structure | | |

<1-4> Preparation of Amorphous Form by t-Butanol/Water

A portion of ED01748-006-001-00 (10 mg) was dissolved in t-butanol (0.2 mL) and water (0.1 mL). A viscous material mixture (ED01748-013-002-00) was provided by flash freezing in a dry ice/acetone bath and freeze-drying the prepared solution. It was confirmed that the result of XRPD analysis corresponds to Pattern 1 (FIG. 3).

<1-5> Preparation of Amorphous Form by Evaporation of DCM Solution

Figure 4:
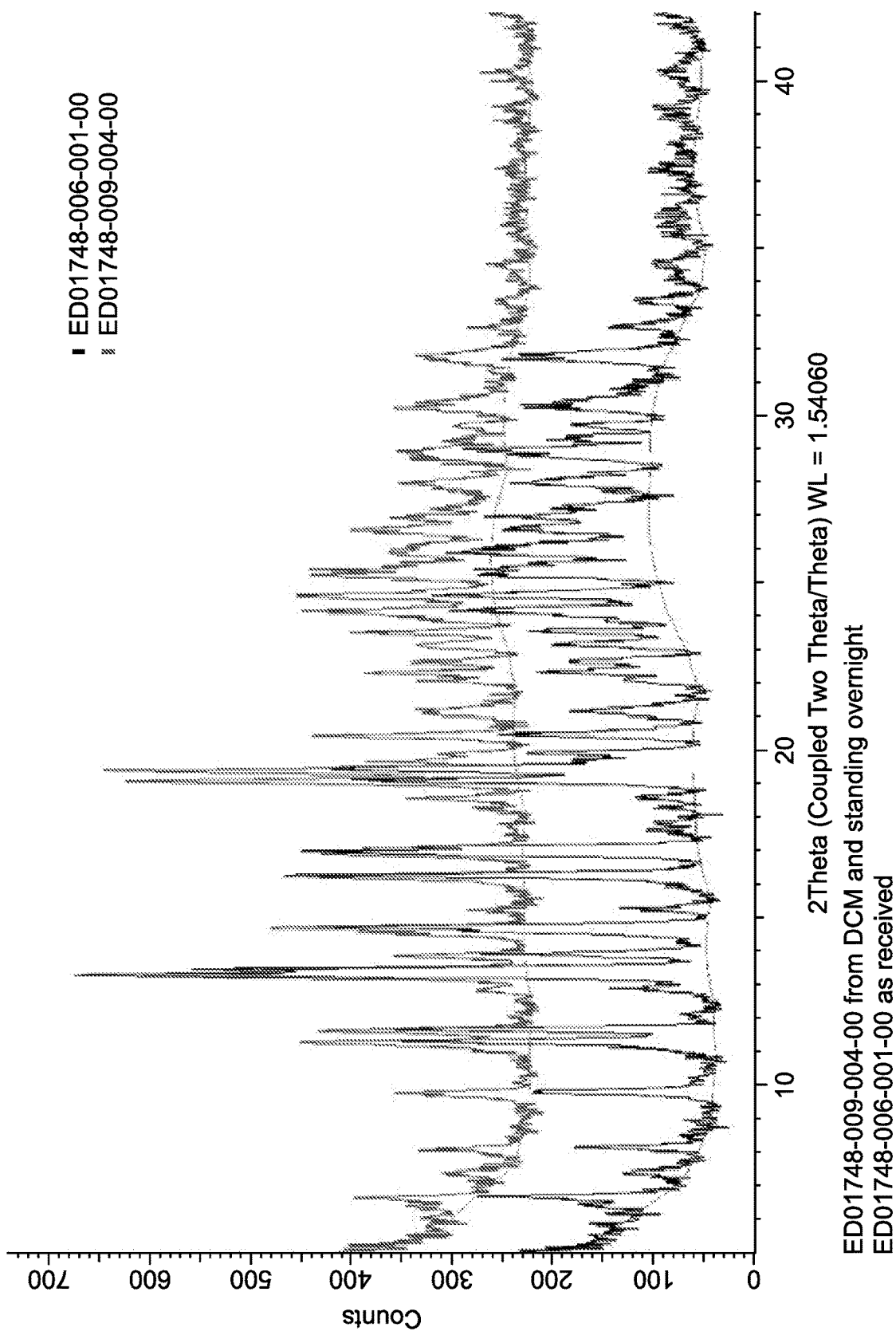
FIG. 4 shows the result of comparing XRPD patterns of a material (ED01748-013-002-00, Pattern 1) formed by treatment of a dichloroform solution and evaporation of the solution to form amorphous 1-(2-chlorophenyl)-(S)-1-hydroxypropyl-(S)-2-carbamate (JBPOS0101).

A portion of ED01748-006-001-00 (20 mg) was dissolved in dichloromethane (DCM)(2 mL), and then the solution was rapidly evaporated under vacuum, thereby obtaining a colorless viscous material. After standing overnight, the total sample was solidified (ED01748-009-004-00), and it was confirmed that the XRPD analysis result corresponds to Pattern 1 (FIG. 4).

<1-6> DSC Experiment for Preparing Amorphous Material

To prepare and confirm an amorphous material, two types of DSC experiments (A/B) were performed on ED01748-006-001-00.

DSC a Experiment

Figure 5:
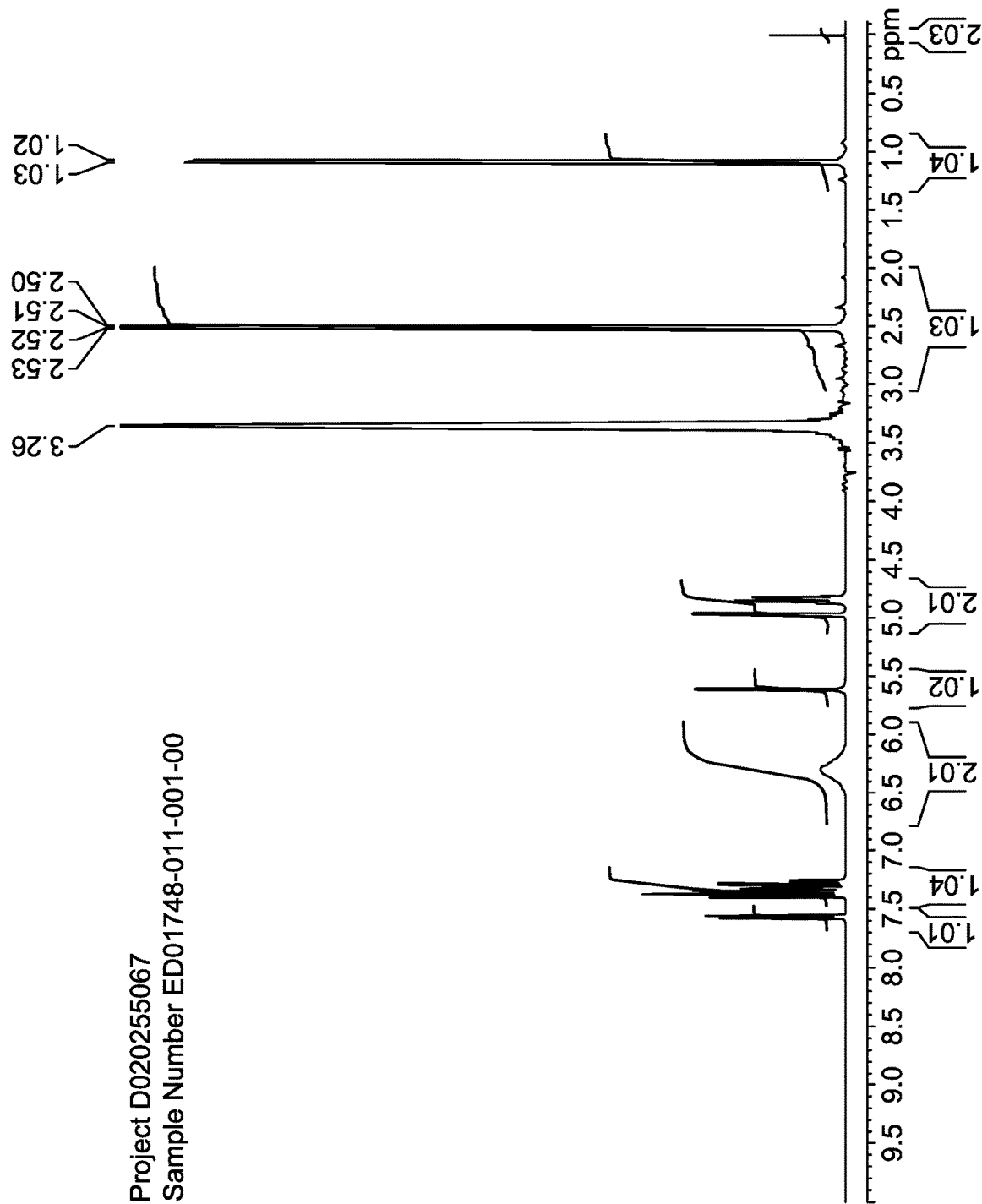
FIG. 5 shows the $^1$H NMR result for a crystal generated after two types of DSC A to prepare and confirm an amorphous material.

A portion of ED01748-006-001-00 was heated in a differential scanning calorimeter at 10° C./min to 110° C., and then cooled to 30° C. at 50° C./min. The contents of a DSC pan were analyzed by $^1$H NMR. As a result, after melting and cooling, no degradation or migration of the sample was observed (FIG. 5).

DSC B Experiment

A portion of ED01748-006-001-00 was heated in a differential scanning calorimeter at 10° C./min to 110° C., and then cooled to −30° C. at 10° C./min, followed by heating again to 300° C.

Finally, as the sample was heated, a glass transition temperature (Tg) was observed at 14.6° C. (median: 15.3° C.), and other thermal changes were not observed until the sample was decomposed at about 190° C. or more.

In both DSC experiments A and B, the sample was dissolved and then cooled, thereby generating an amorphous material, and there was no evidence of decomposition by NMR. Experiment B showed a low glass transition temperature (Tg onset: 14.6° C.) of the material, indicating that the stability of the amorphous material may be an issue.

<1-7> Preparation of Amorphous Form by Melting and Rapid Cooling

Figure 6:
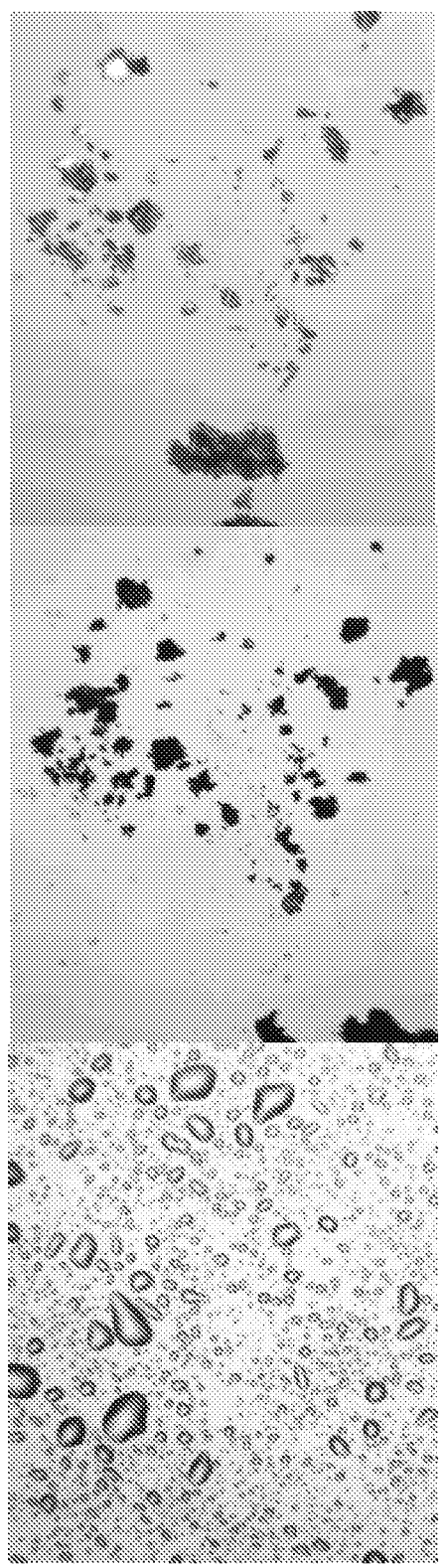
FIG. 6 shows the result of observing crystalline forms formed by melting-rapid cooling and external stimulation using an optical microscope.
Figure 7:
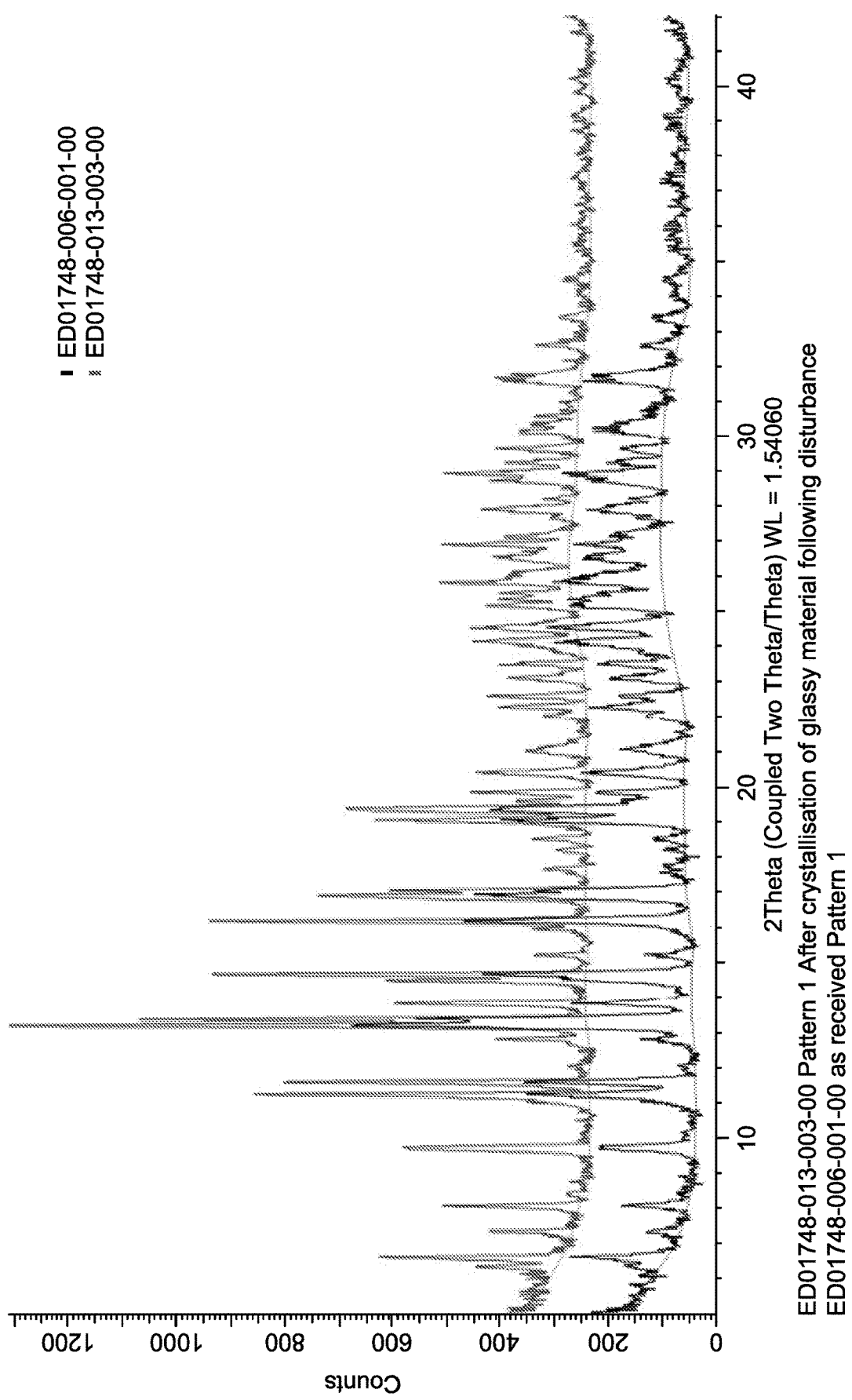
FIG. 7 shows the result of XRPD analysis for a crystalline form formed after melting-rapid cooling and storage.

Each (about 10 mg) of two ED01748-006-001-00 samples was put into a vial, and then into a drying pistol which had been preheated to 110° C. for 10 minutes under ambient pressure. The molten sample was removed, followed by rapid cooling with dry ice. As a result of observation with an optical microscope, glass droplets were observed as shown in FIG. 6. The glass material from the first sample was rapidly crystallized by impacting a part that characterized it. As a result of XRPD analysis, the glass material was identified as Pattern 1 (FIG. 7). The material was not significantly decomposed as confirmed by 41 NMR or UPLC, and the sample had a UPLC purity of 98.7%.

Figure 8:
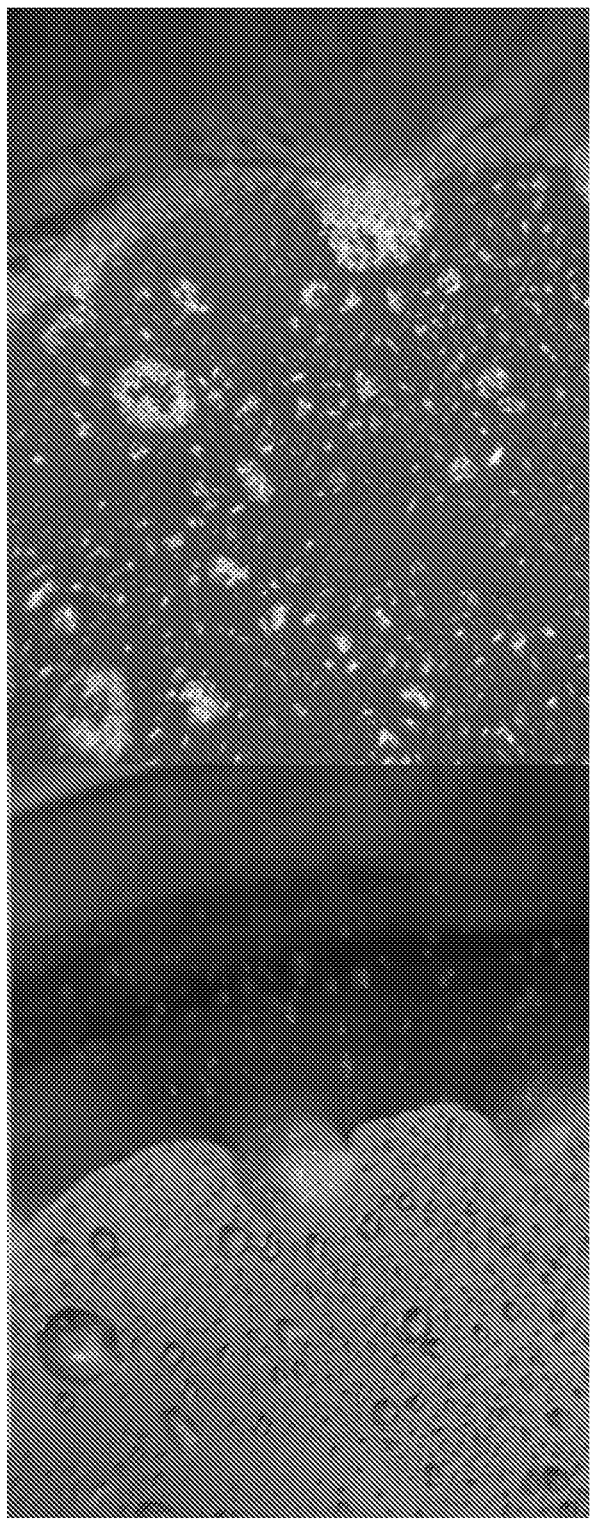
FIG. 8 shows the result of observing a crystalline form formed after melting-rapid cooling and storage using an optical microscope. (overnight (left), 4 days (right))

The second sample of the cooled material was stored in a closed vial overnight and observed using an optical microscope. A very small amount of crystalline material was observed (FIG. 8, left), and after standing for 4 days, it was confirmed that the material was completely crystallized (FIG. 8, right).

<Example 2> Preparation of Pattern 1 Crystalline Form of Amorphous 1-(2-chlorophenyl)-(S)-1-hydroxypropyl-(S)-2-carbamate using solvent A polymorphic pattern of the amorphous 1-(2-chlorophenyl)-(S)-1-hydroxypropyl-(S)-2-carbamate obtained in Example 1 was confirmed using various solvents (mainly ICH Class II and III).

A portion (each 10 mg) of ED01748-006-001-00 was dispensed into a vial, and an open vial was melted in a drying pistol (preheated at 110° C.) for 10 minutes under ambient pressure. The molten sample was removed, followed by rapid cooling with dry ice. The resulting amorphous glass material was treated with one solvent selected from acetone, chloroform, methanol (MeOH), tetrahydrofuran, diisopropyl ether, ethanol (EtOH), methyl ethyl ketone, acetonitrile, 2-propanol, tert-butanol, 1,2-dimethoxyethane (DME), 1-propanol, 2-butanol, water, 1,4-dioxane, 2-methyl-1-propanol, 2-methoxyethanol, butyl acetate, methyl butyl ketone, 3-methyl-1-butanol, 1-pentanol, cumene and anisole. The sample was shaken at room temperature for 2 to 3 hours, and then solvents except t-BuOH and 1,4-dioxane were transferred to a refrigerator. The other samples were stirred overnight at room temperature.

All solid samples were analyzed using an optical microscope and XRPD. In the experiment, most of the solutions were stored in a refrigerator for 2 days, and the remaining solutions were removed with CHCl$_3$ and anisole by evaporation at room temperature. CHCl$_3$ provided a solid rapidly dissolved by evaporating the resulting solution before isolation, and anisole provided a solid dissolved at room temperature before isolation, thereby obtaining a solid after partial evaporation. The residual solid obtained by evaporation was analyzed using an optical microscope and XRPD.

Figure 9:
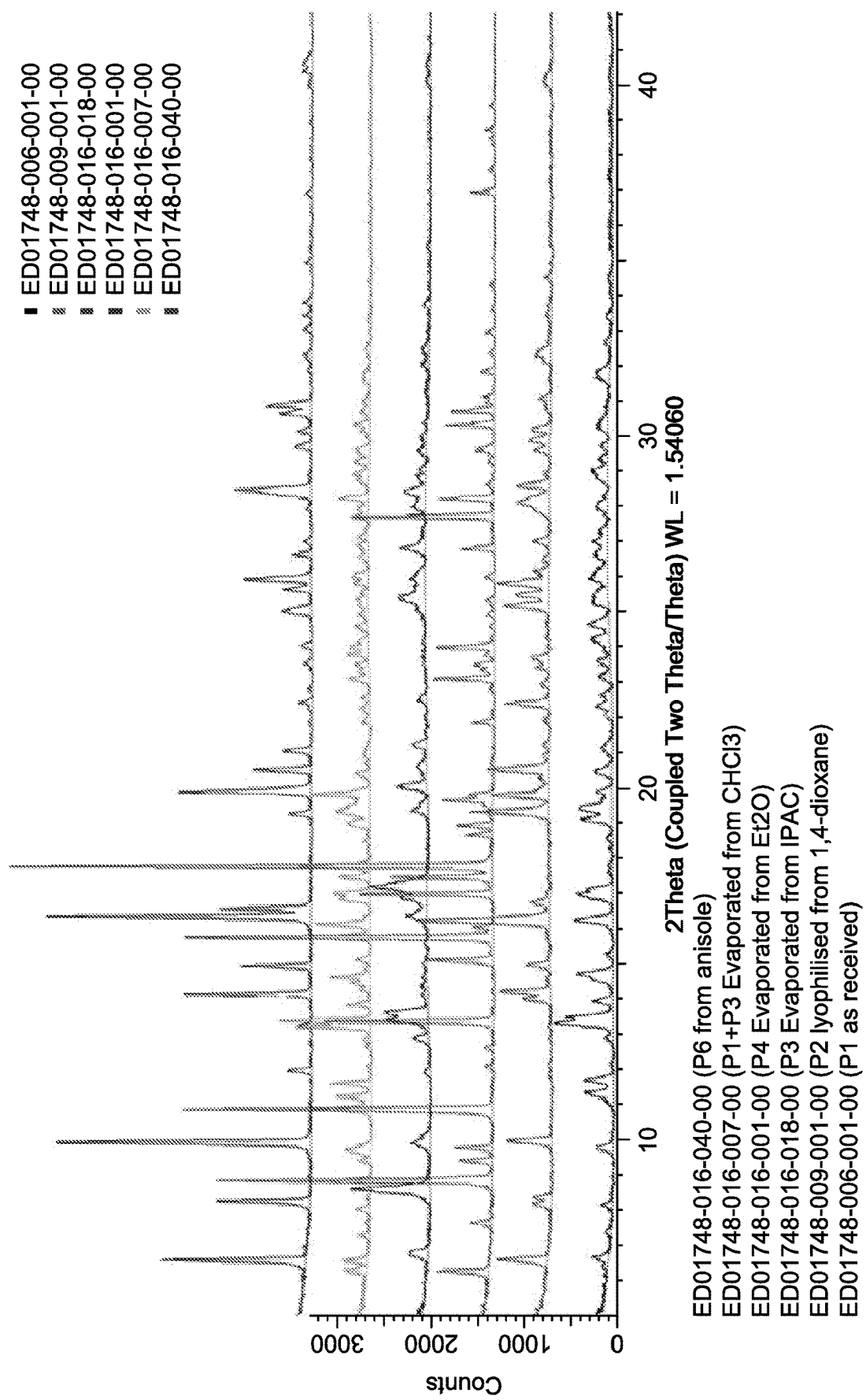
FIG. 9 shows the overlaid XRPD diffractogram results of crystalline forms of amorphous Pattern 1, 2, 3, 4 and 6.

As a result, from most of the solvents, Pattern 1 or Pattern 3 was confirmed, Pattern 4 was confirmed from diethyl ether, a mixture of Pattern 1 and Pattern 3 was confirmed from chloroform and propyl acetate, Pattern 6 was confirmed from toluene and anisole, and a mixture of Pattern 3 and Pattern 6 was confirmed from benzonitrile. It was observed that the Pattern 6 material confirmed from toluene was converted to a mixture of Pattern 6 and Pattern 3 by XRPD. The Pattern 6 material confirmed from anisole stood overnight, and then converted to a mixture of Pattern 6 and Pattern 1 by XRPD. The various XRPD diffraction patterns obtained as above are shown in FIG. 9.

<Experimental Example 1> Analysis of Crystalline form Pattern 1 (ED01748-006-001-00) of (1-(2-chlorophenyl)-(S)-1-hydroxypropyl-(S)-2-carbamate)

Figure 10:
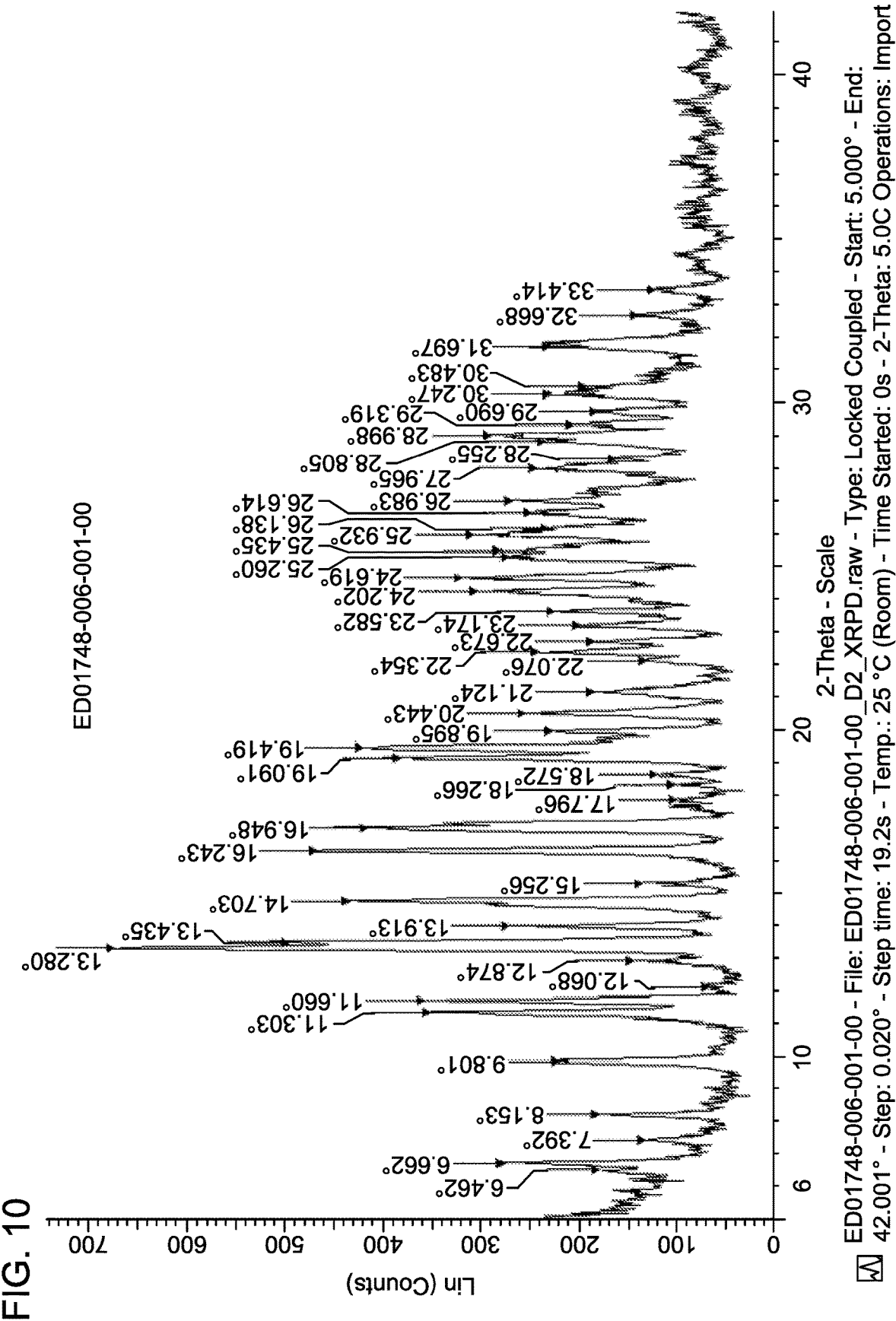
FIG. 10 shows the XRPD diffractogram result of the crystalline form of 1-(2-chlorophenyl)-(S)-1-hydroxypropyl-(S)-2-carbamate (JBPOS0101) Pattern 1.

A crystalline form of 1-(2-chlorophenyl)-(S)-1-hydroxypropyl-(S)-2-carbamate (JBPOS0101/S-P-17001) obtained from Bio-Pharm Solutions Co. Ltd., analyzed by XRPD, is shown in FIG. 10 and Table 2 below, which is defined as Pattern 1.

TABLE 2

| Caption | Angle 2-Theta° | d value Angstrom | Intensity Count | Intensity % |
|---|---|---|---|---|
| 6.662° | 6.662 | 13.25637 | 275 | 40.7 |
| 7.392° | 7.392 | 11.94899 | 132 | 19.6 |
| 8.153° | 8.153 | 10.83624 | 179 | 26.5 |

TABLE 2-continued

| Caption | Angle 2-Theta° | d value Angstrom | Intensity Count | Intensity % |
|---|---|---|---|---|
| 9.801° | 9.801 | 9.01695 | 219 | 32.4 |
| 11.303° | 11.303 | 7.8224 | 351 | 52 |
| 11.660° | 11.66 | 7.5835 | 357 | 52.9 |
| 12.068° | 12.068 | 7.32802 | 66 | 9.8 |
| 12.874° | 12.874 | 6.8707 | 144 | 21.3 |
| 13.280° | 13.28 | 6.66182 | 675 | 100 |
| 13.435° | 13.435 | 6.58531 | 496 | 73.5 |
| 13.913° | 13.913 | 6.36017 | 271 | 40.1 |
| 14.703° | 14.703 | 6.02005 | 434 | 64.3 |
| 15.256° | 15.256 | 5.80305 | 135 | 20 |
| 16.243° | 16.243 | 5.45254 | 467 | 69.2 |
| 16.948° | 16.948 | 5.22742 | 415 | 61.5 |
| 17.796° | 17.796 | 4.98008 | 99 | 14.7 |
| 18.266° | 18.266 | 4.85289 | 101 | 15 |
| 18.572° | 18.572 | 4.77361 | 119 | 17.6 |
| 19.091° | 19.091 | 4.64505 | 382 | 56.6 |
| 19.419° | 19.419 | 4.56748 | 420 | 62.2 |
| 19.895° | 19.895 | 4.45926 | 226 | 33.5 |
| 20.443° | 20.443 | 4.34088 | 254 | 37.6 |
| 21.124° | 21.124 | 4.20246 | 184 | 27.3 |
| 22.076° | 22.076 | 4.02326 | 131 | 19.4 |
| 22.354° | 22.354 | 3.97388 | 240 | 35.6 |
| 22.673° | 22.673 | 3.91877 | 184 | 27.3 |
| 23.174° | 23.174 | 3.83509 | 198 | 29.3 |
| 23.582° | 23.582 | 3.76964 | 224 | 33.2 |
| 24.202° | 24.202 | 3.67451 | 303 | 44.9 |
| 24.619° | 24.619 | 3.6132 | 319 | 47.3 |
| 25.260° | 25.26 | 3.52298 | 271 | 40.1 |
| 25.435° | 25.435 | 3.49906 | 279 | 41.3 |
| 25.932° | 25.932 | 3.43308 | 307 | 45.5 |
| 26.138° | 26.138 | 3.40653 | 230 | 34.1 |
| 26.614° | 26.614 | 3.34669 | 248 | 36.7 |
| 26.983° | 26.983 | 3.30175 | 268 | 39.7 |
| 27.965° | 27.965 | 3.18799 | 243 | 36 |
| 28.256° | 28.256 | 3.15585 | 161 | 23.9 |
| 28.805° | 28.805 | 3.09686 | 234 | 34.7 |
| 28.998° | 28.998 | 3.07672 | 289 | 42.8 |
| 29.319° | 29.319 | 3.0438 | 206 | 30.5 |
| 29.690° | 29.69 | 3.00656 | 180 | 26.7 |
| 30.247° | 30.247 | 2.95246 | 229 | 33.9 |
| 30.483° | 30.483 | 2.93017 | 192 | 28.4 |
| 31.697° | 31.697 | 2.82066 | 228 | 33.8 |
| 32.668° | 32.668 | 2.73894 | 140 | 20.7 |
| 33.414° | 33.414 | 2.67953 | 121 | 17.9 |

The features of Pattern 1 were confirmed as follows.

TABLE 3

| Pattern | Features |
|---|---|
| Pattern 1 (anhydrous) | Endothermic events of Onset 81° C. (small amount) and 89° C. No mass loss in TGA upon decomposition. In polymorphic screening, can be obtained when various solvents were added to an amorphous form, and have partially improved crystallinity (ED01748-016-014-00 of MeCN, ED01748-016-010-00 of DIPE). No low temperature endothermic event. |

Figure 11:
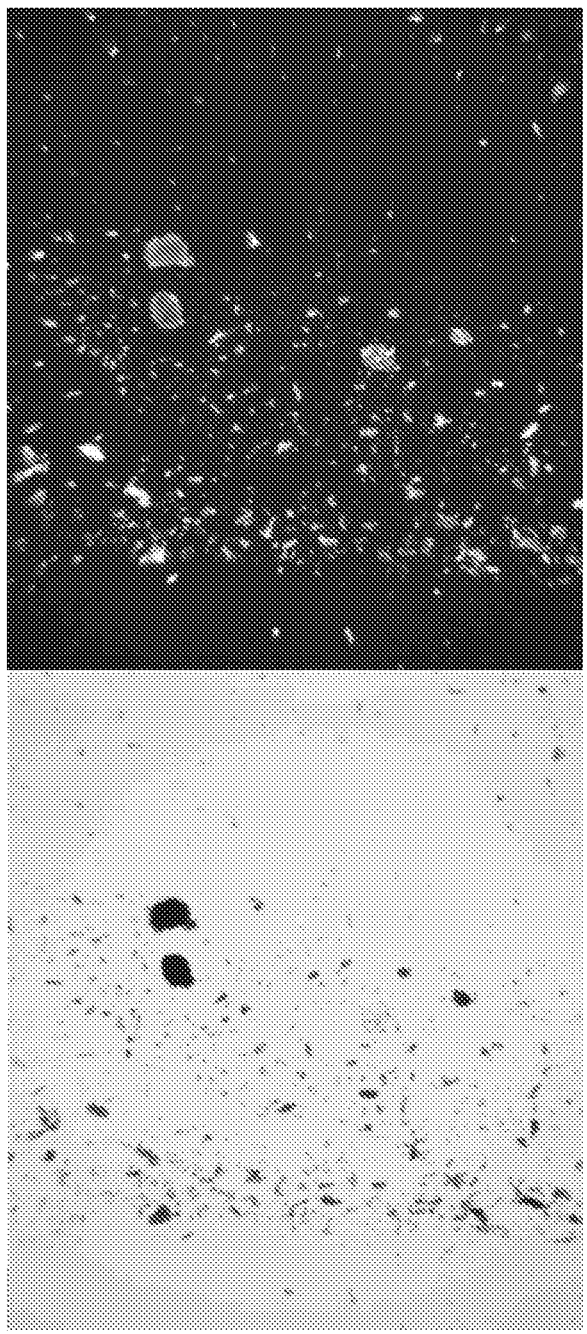
FIG. 11 shows the optical microscope images of the crystalline form of 1-(2-chlorophenyl)-(S)-1-hydroxypropyl-(S)-2-carbamate (JBPOS0101) Pattern 1.
Figure 12:
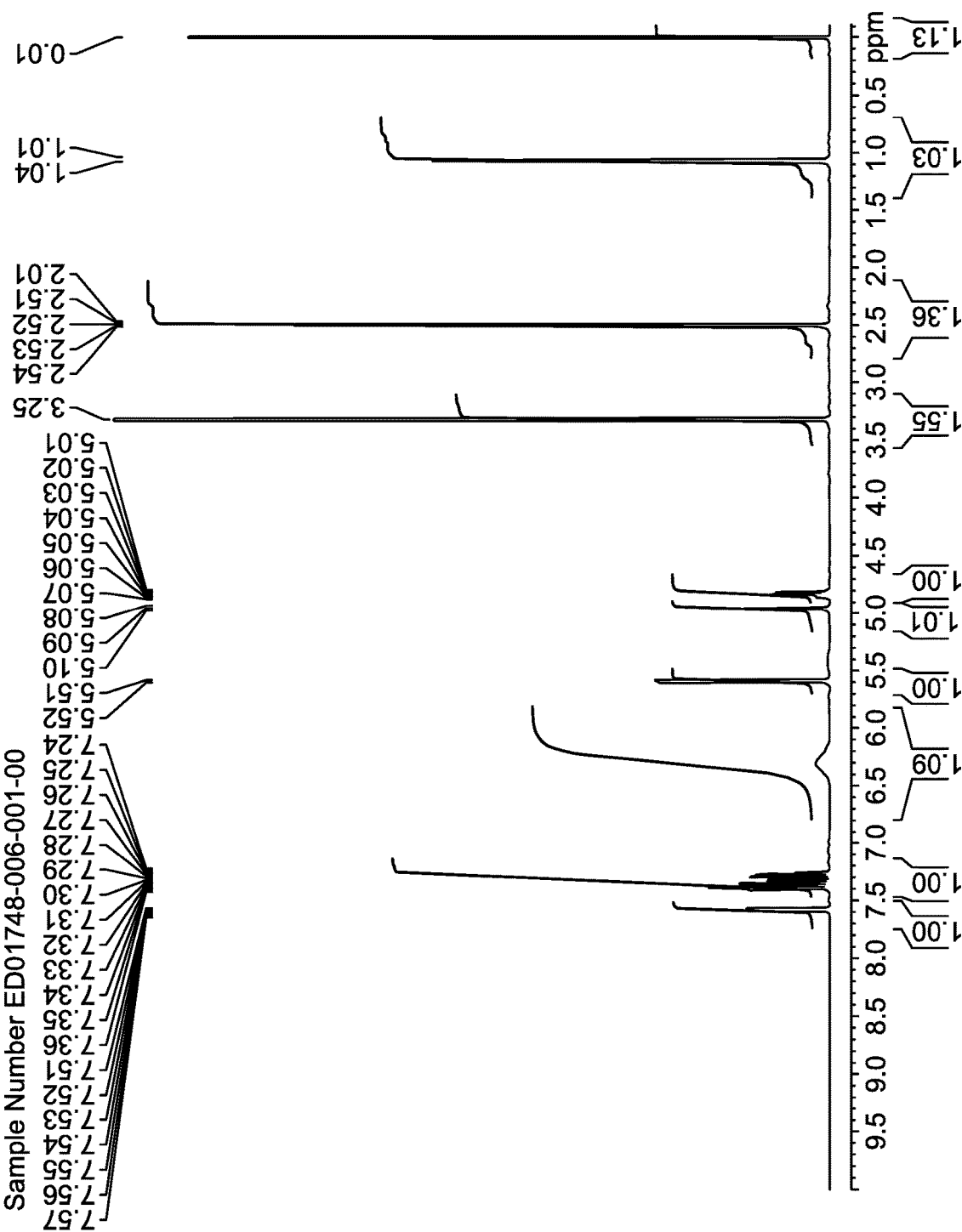
FIG. 12 shows the $^1$H NMR result of the crystalline form of 1-(2-chlorophenyl)-(S)-1-hydroxypropyl-(S)-2-carbamate (JBPOS0101) Pattern 1.
Figure 13:
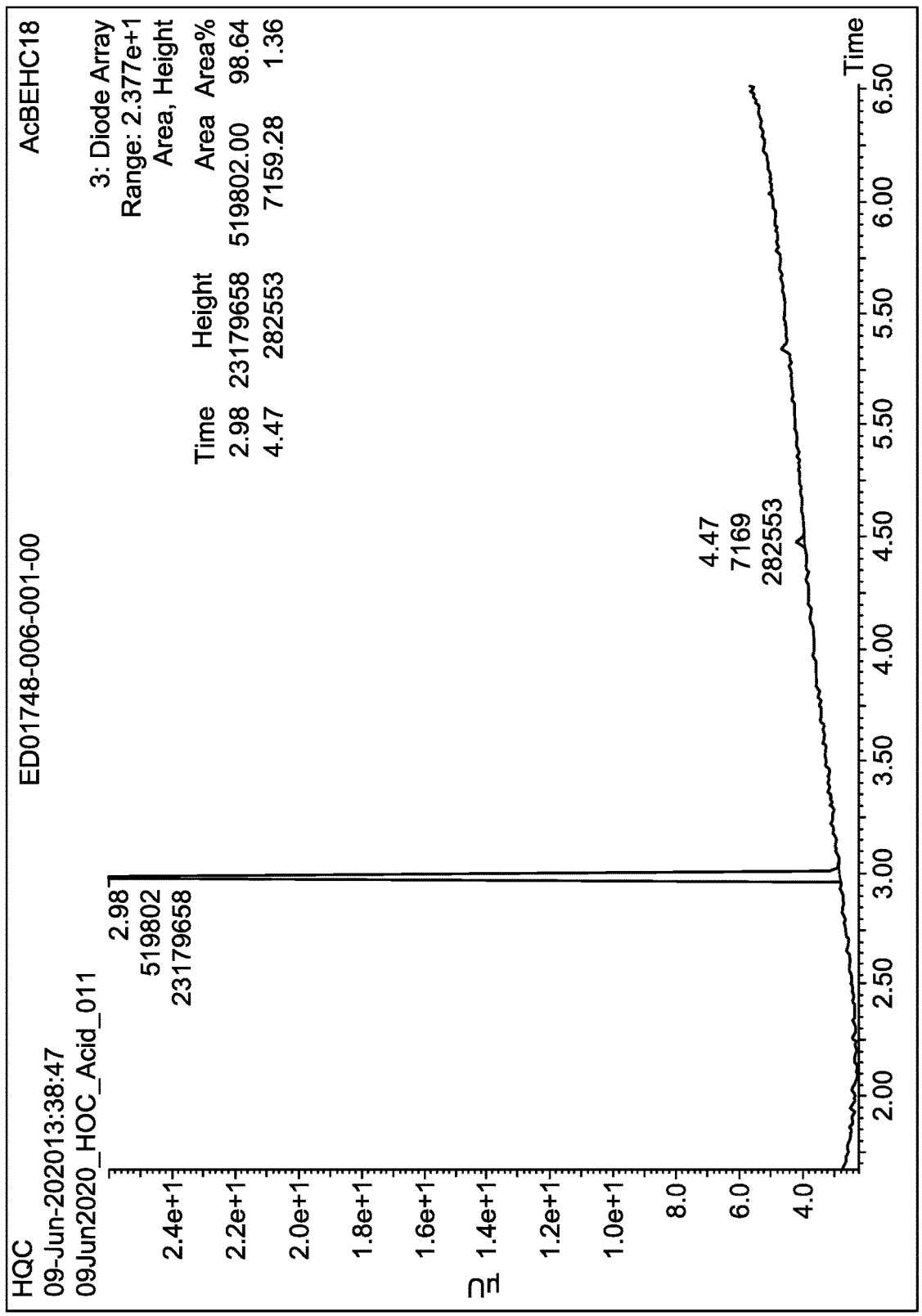
FIG. 13 shows the UV detection chromatogram result obtained by measuring the UPLC purity of the crystalline form of 1-(2-chlorophenyl)-(S)-1-hydroxypropyl-(S)-2-carbamate (JBPOS0101) Pattern 1.

The optical microscope images of the crystallized ED01748-006-001-00 Pattern 1 are shown in FIG. 11. In addition, the $^1$H NMR analysis result of the ED01748-006-001-00 corresponded to the structure shown in FIG. 12. In addition, the UPLC purity was 98.6%, as determined by a UV detection chromatogram (FIG. 13).

Figure 14:
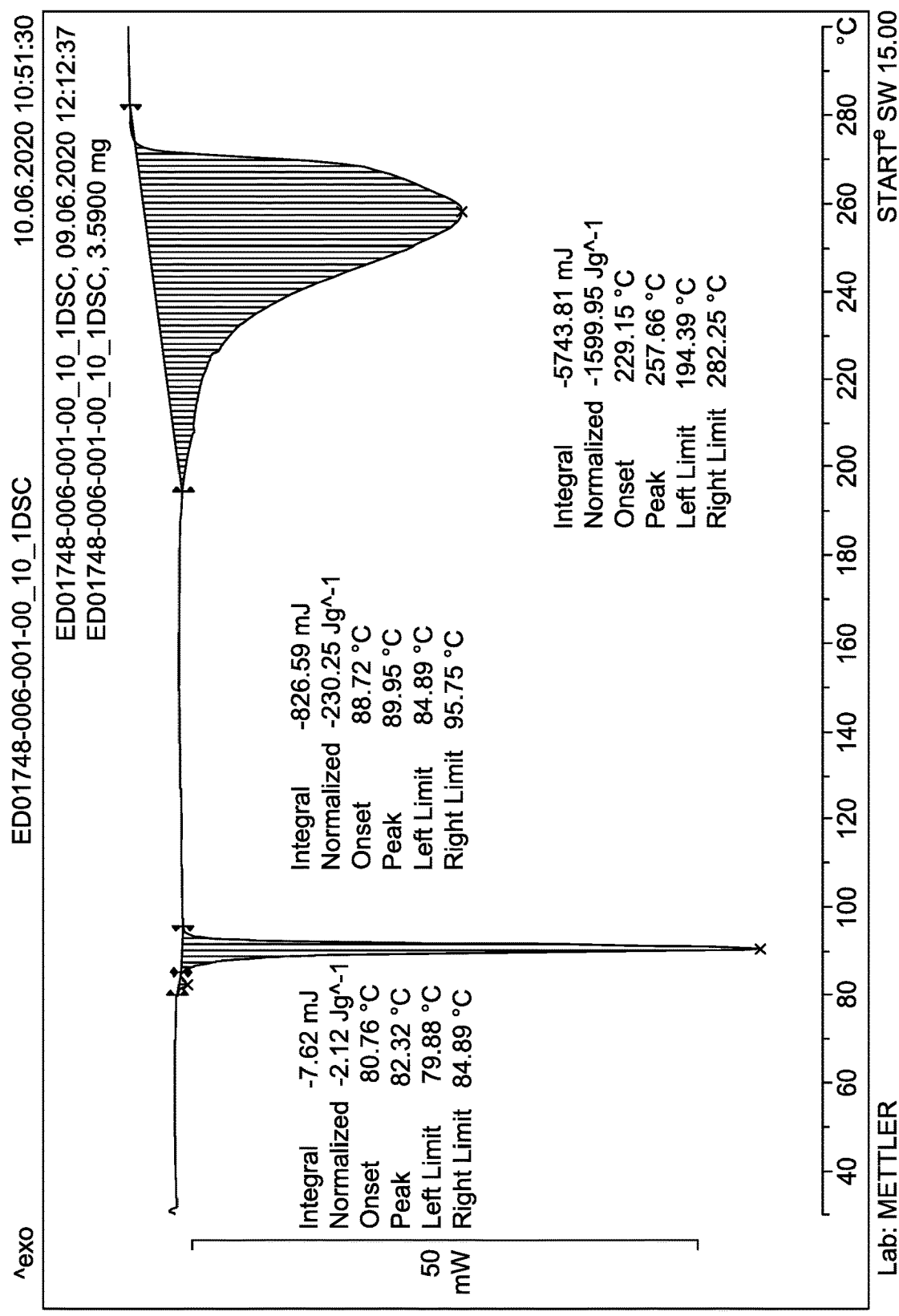
FIG. 14 is the DSC thermogram of the crystalline form of 1-(2-chlorophenyl)-(S)-1-hydroxypropyl-(S)-2-carbamate (JBPOS0101) Pattern 1.

In addition, as a result of thermal analysis of ED01748-006-001-00 by DSC, it was confirmed that a small endothermic reaction started at 81° C. (peak 82° C.), and an endothermic reaction started at 89° C. (peak 90° C.) corresponding to a melting temperature (FIG. 14).

Figure 15:
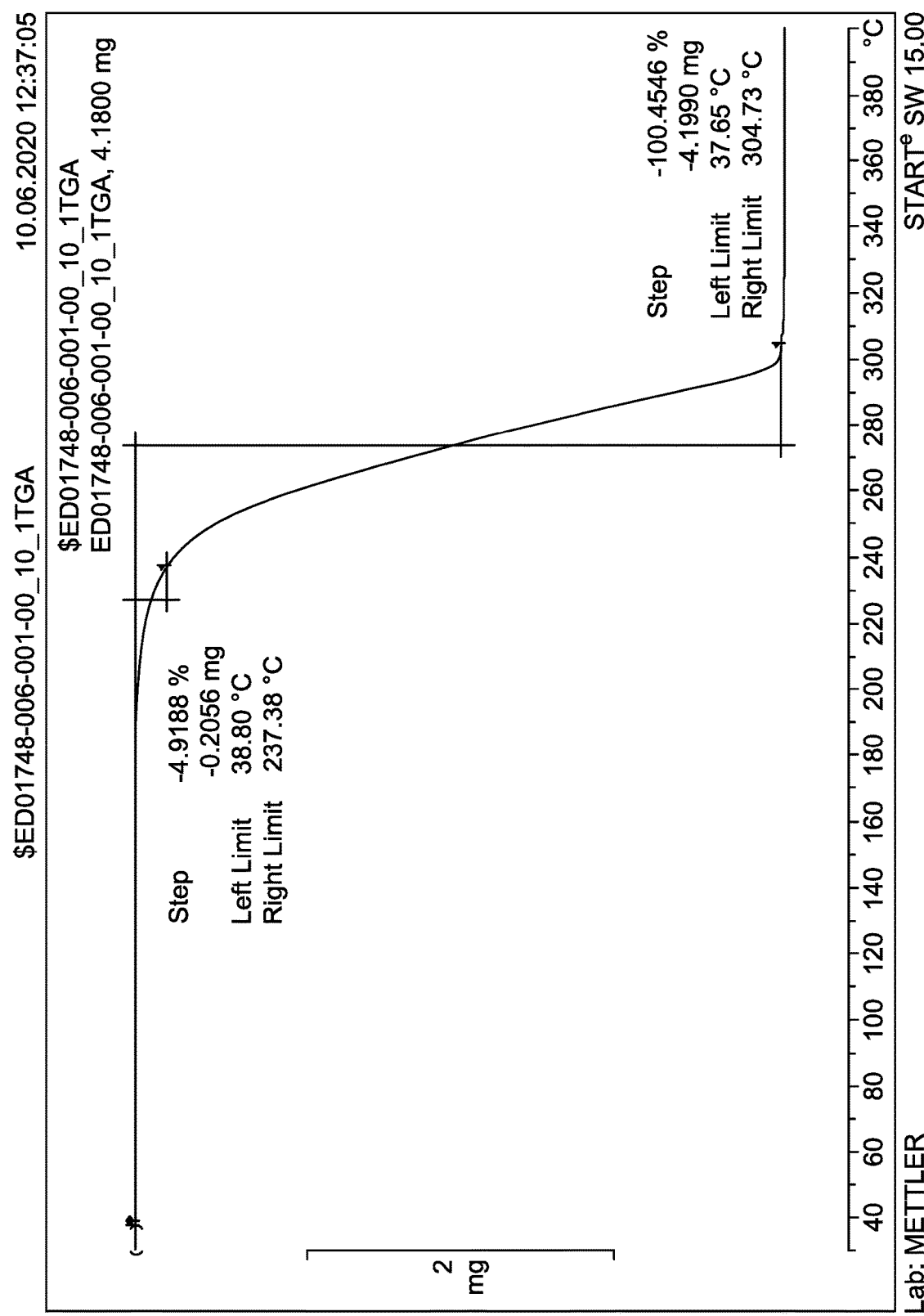
FIG. 15 is the TGA thermogram of the crystalline form of 1-(2-chlorophenyl)-(S)-1-hydroxypropyl-(S)-2-carbamate (JBPOS0101) Pattern 1 at a temperature of 200° C. or more.

In addition, at temperatures of about 200° C. or more, a broad peak corresponding to a mass loss observed by TGA through decomposition was shown at 229° C. TGA shows that 95% of the mass remained even at 237° C. without considerable mass loss until a temperature exceeded about 200° C. 100% of the mass was lost at 305° C. (FIG. 15).

Figure 16:
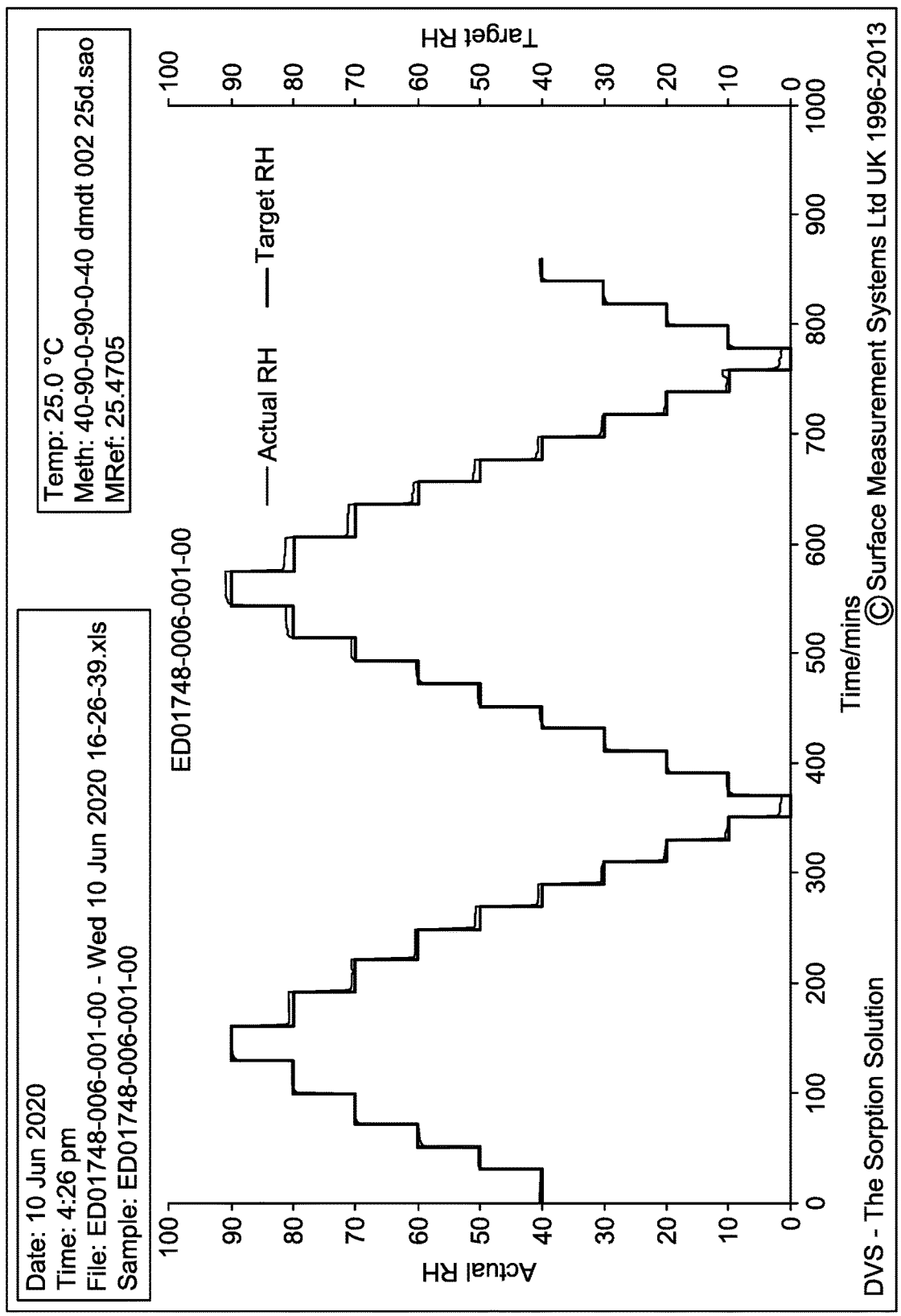
FIG. 16 shows the GVS change in the mass plot of the crystalline form of 1-(2-chlorophenyl)-(S)-1-hydroxypropyl-(S)-2-carbamate (JBPOS0101) Pattern 1.
Figure 17:
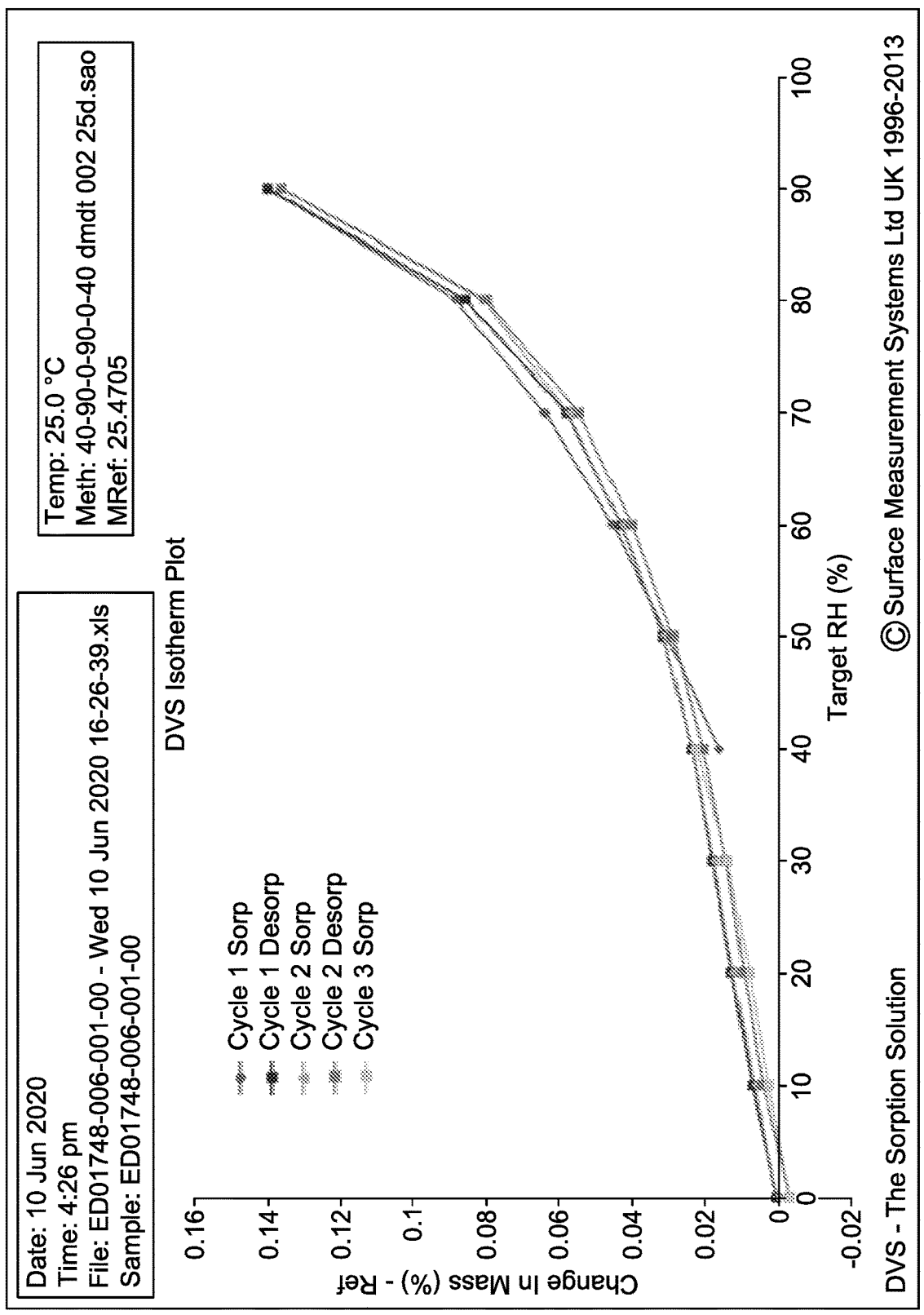
FIG. 17 shows the GVS isotherm plot of the crystalline form of 1-(2-chlorophenyl)-(S)-1-hydroxypropyl-(S)-2-carbamate (JBPOS0101) Pattern 1.

From the GVS experiment result, the ED01748-006-001-00 also showed that the mass was increased by 0.14% in a range of 0 to 90% relative humidity (R.H.) like the isotherm plot of FIG. 16. This means that a mass increase is insignificant, which shows storage stability by humidity is improved (FIGS. 16 and 17).

Figure 18:
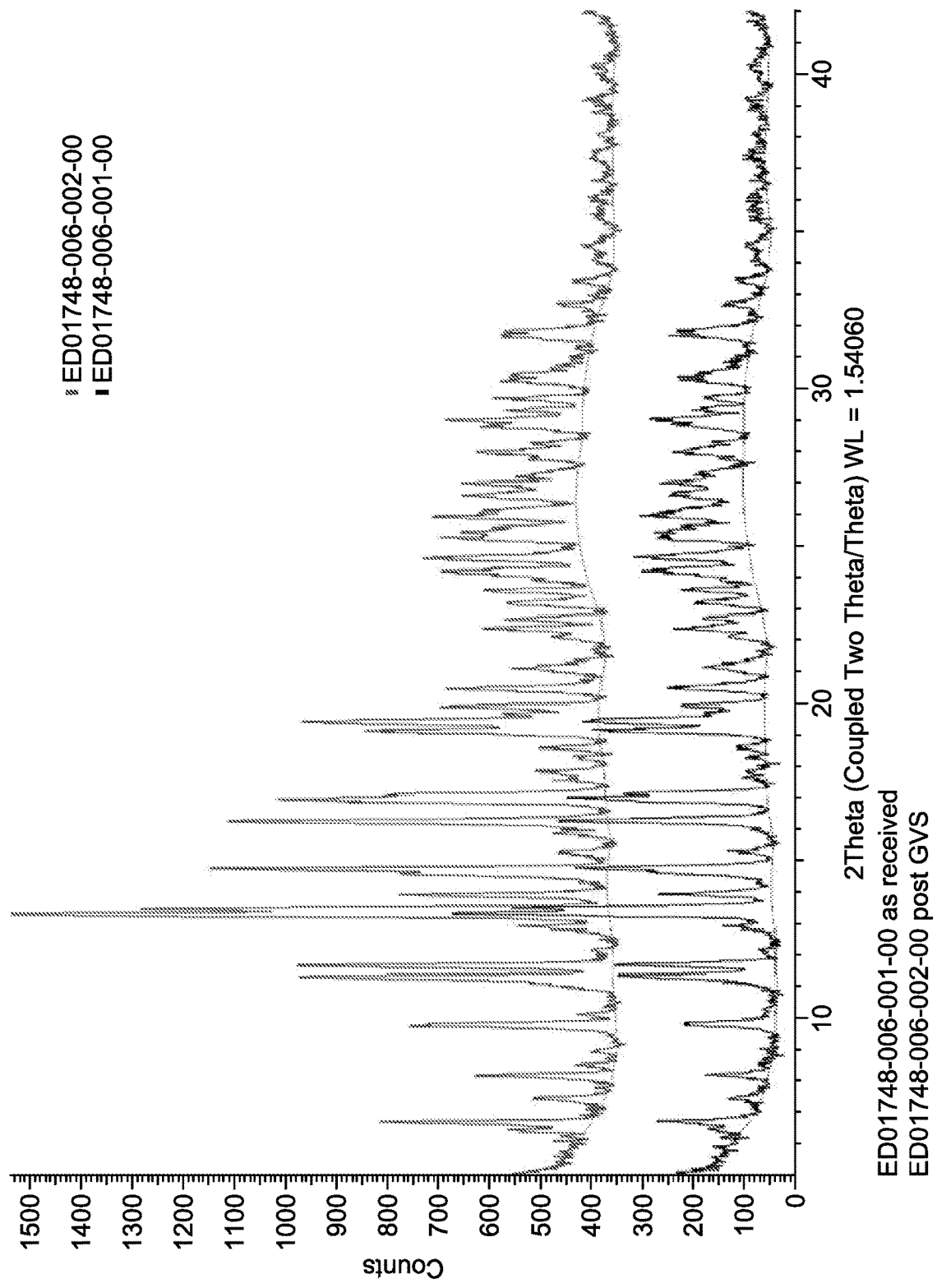
FIG. 18 shows the XRPD analysis result for the crystalline form of 1-(2-chlorophenyl)-(S)-1-hydroxypropyl-(S)-2-carbamate before and after GVS.
Figure 19:
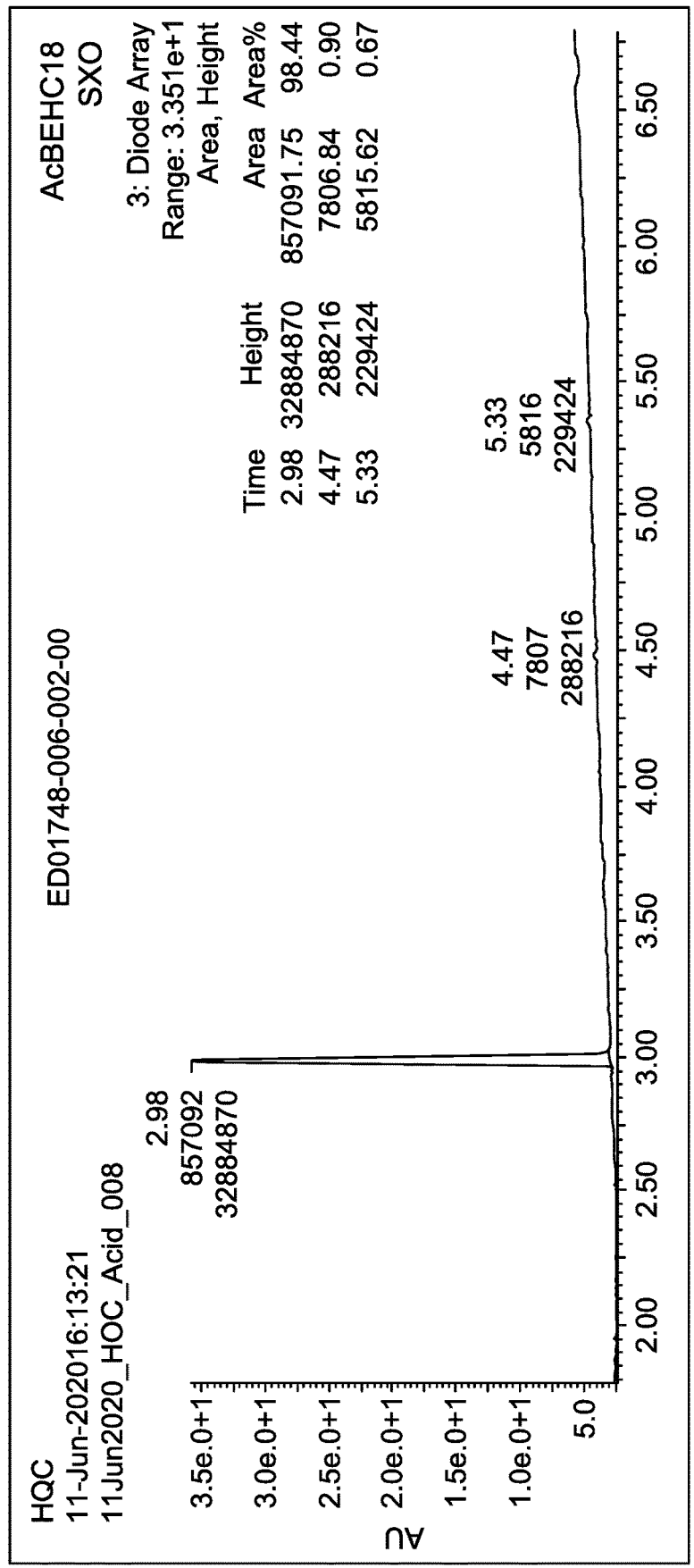
FIG. 19 shows the result of observing the change in purity before and after GVS through UPLC.

After the GVS experiment, there was no change in morphology observed from the XRPD result. When the ED01748-006-001-00 was stored under a stress condition of 40° C./75% RH or RT/97% RH, no change in morphology by XRPD was shown (FIG. 18). In addition, it was observed that the change in purity was 97.4% after 40° C./75% RH and 97.7% after RT/97% RH by UPLC (FIG. 19).

<Experimental Example 2> Measurement of solubility of Crystalline Form (ED01748-006-001-00) Pattern 1 of (1-(2-chlorophenyl)-(S)-1-hydroxypropyl-(S)-2-carbamate)

To measure the solubility of ED01748-006-001-00 Pattern 1, experiments were carried out in biological media (Fasted simulated gastric fluid (FaSSGF) and Fasted simulated intestinal fluid (FaSSIF)) at 37° C. 10 mL each of samples was dispersed into each of four vials, 1 mL each of FaSSGF and FaSSIF was added to each of the two vials and incubated in an orbital shaker for 24 hours. After incubation, all solids in each sample were dissolved, and the solubility was measured as follows.

TABLE 4

| Sample | FaSSGF solubility after 24 h | FaSSIF solubility after 24 h |
|---|---|---|
| ED01748-006-001-00 | 16.84 mg/mL | 14.05 mg/mL |

<Experimental Example 3> Confirmation of Thermodynamic Stability of Crystalline Form Pattern 1 of (1-(2-chlorophenyl)-(S)-1-hydroxypropyl-(S)-2-carbamate)

<3-1> Competitive slurry experiment for Pattern 1 and Pattern 3

To investigate the relative thermodynamic stability of various crystalline form patterns at room temperature and 50° C., competitive slurry experiments were carried out.

A mixture of Pattern 1 and Pattern 3 (ED01748-028-003-00, 4×20 mg) was dispensed into vials. They were treated with 250 μL of a saturated solution of Pattern 1 (ED01748-006-001-00) in DIPE or heptane (50 mg of ED01748-006-001-00 was treated with DIPE or heptane and heated at 50° C., a portion was removed as needed, and the resulting product was filtered through a 0.45 μm syringe filter, thereby forming a slurry). The produced slurry was stirred at room temperature or 50° C. A small sample was periodically removed and analyzed by XRPD, followed by monitoring the progress as shown in the following table. After analysis, the solid was returned to the vial, and an additional saturated solution was added as needed to maintain the slurry. After 4 days, the purity of the material was confirmed by UPLC. In both of DIPE samples, the purity was decreased to 98%, and in a heptane sample, the purity was 98.5%.

TABLE 5

| Experiment | Solvent | Conditions | Time | Result |
|---|---|---|---|---|
| ED01748-033-001 | DIPE | RT | 1 day | P1 |
| ED01748-033-002 | DIPE | 50° C. | 1 day | P1 |
| ED01748-033-003 | Heptane | RT | 1 day | P1 + P3 |
| ED01748-033-004 | Heptane | 50° C. | 1 day | P1 + P3 |
| ED01748-042-005 | DIPE | RT | 4 days | P1 |
| ED01748-042-006 | DIPE | 50° C. | 4 days | P1 |
| ED01748-042-007 | Heptane | RT | 4 days | P1 + P3 |
| ED01748-042-008 | Heptane | 50° C. | 4 days | P1 |
| ED01748-042-009 | Heptane | RT | 11 days | P1 |

Figure 20:
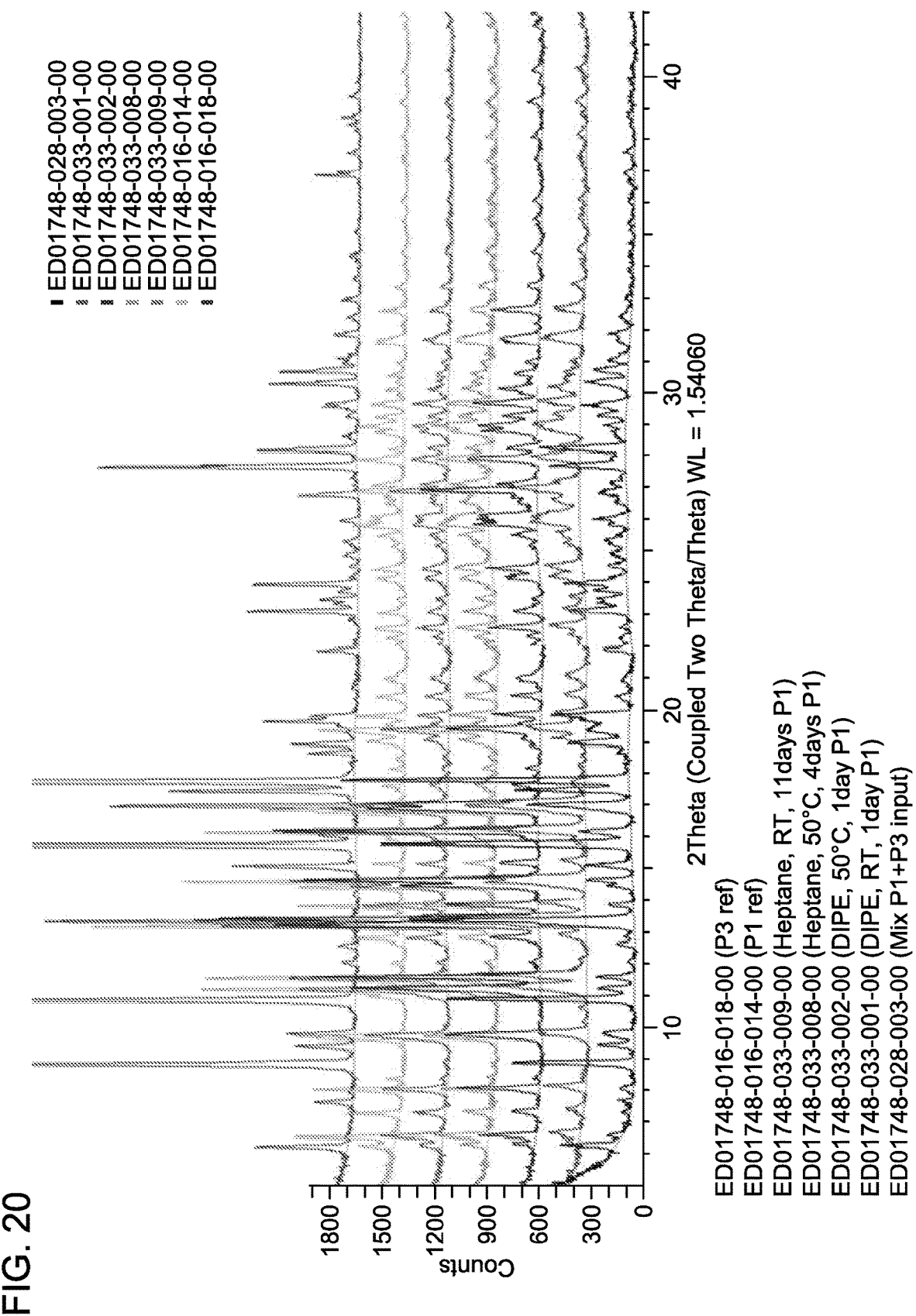
FIG. 20 is the result of forming a competitive slurry, obtained by overlaying XRPD patterns for crystalline forms of Pattern 1 and Pattern 3 and a mixture thereof after DIPE and heptane treatment.

The XRPD result of the material in this table is shown in FIG. 20. In DIPE and heptane, both types of competitive slurries of the mixture of Pattern 1 and Pattern 3, which are anhydrous, were converted to Pattern 1 at room temperature and 50° C., and XRPD showed that no Pattern 3 remains. In heptane, the conversion to Pattern 1 was slower than that of DIPE, which is caused by a difference in solubility of materials. From the result, it was confirmed that Pattern 1 is more thermodynamically stable than Pattern 3.

<3-2> Competitive Slurry Experiment for Pattern 1, Pattern 3, Pattern 6 and Pattern 11

A mixture of Pattern 1 and Pattern 3 (ED01748-028-003-00, 10 mg each) was dispensed into four vials, and Pattern 6 (ED01748-034-002-00, 5 mg) and Pattern 11 (ED01748-037-002-00, 5 mg) were added to respective vials. Each sample was treated with 300 µL of a filtered saturated solution of Pattern 1 (ED01748-006-001-00) prepared in DIPE or heptane. The resulting slurries were stirred at room temperature and 50° C. A small sample was periodically removed and analyzed by XRPD, followed by monitoring as described in the following table.

After analysis, the solid was returned to the vial, and a saturated solution was additionally injected as needed to maintain the slurries. After 25 days, the purity of the solid material obtained in the heptane experiment was confirmed by UPLC, and no significant decrease in purity was shown by UPLC.

TABLE 6

| Experiment | Solvent | Conditions | Time | Result |
|---|---|---|---|---|
| ED01748-042-001 | DIPE | RT | 1 day | P1 |
| ED01748-042-002 | DIPE | 50° C. | 1 day | P1 |
| ED01748-042-003 | Heptane | RT | 1 day | P1 + P11 |
| ED01748-042-004 | Heptane | 50° C. | 1 day | P1 + P11 |
| ED01748-042-005 | Heptane | RT | 5 days | P1 + P11 |
| ED01748-042-006 | Heptane | 50° C. | 5 days | P1 + P11 |
| ED01748-042-007 | Heptane | RT | 11 days | P1 + P11 |
| ED01748-042-008 | Heptane | 50° C. | 11 days | P1 + P11 |
| ED01748-042-009 | Heptane | RT | 25 days | P1 + P11 |
| ED01748-042-010 | Heptane | 50° C. | 25 days | P1 + P11 |

Figure 21:
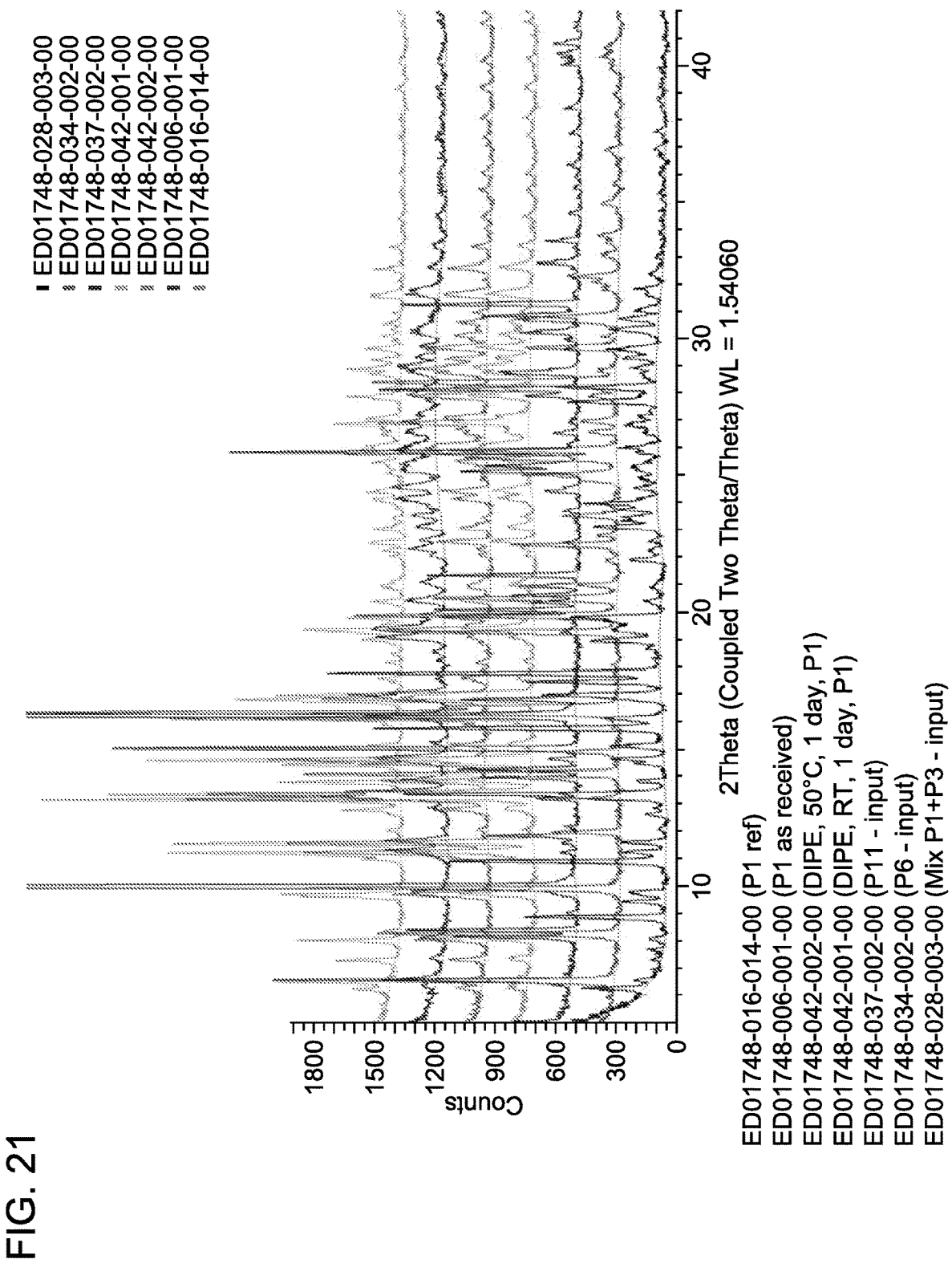
FIG. 21 and FIG. 22 are the results of forming a competitive slurry, obtained by overlaying XRPD patterns for crystalline forms of Pattern 1, Pattern 3, Pattern 6 and Pattern 11 or a mixture thereof after DIPE and heptane treatment.
Figure 22:
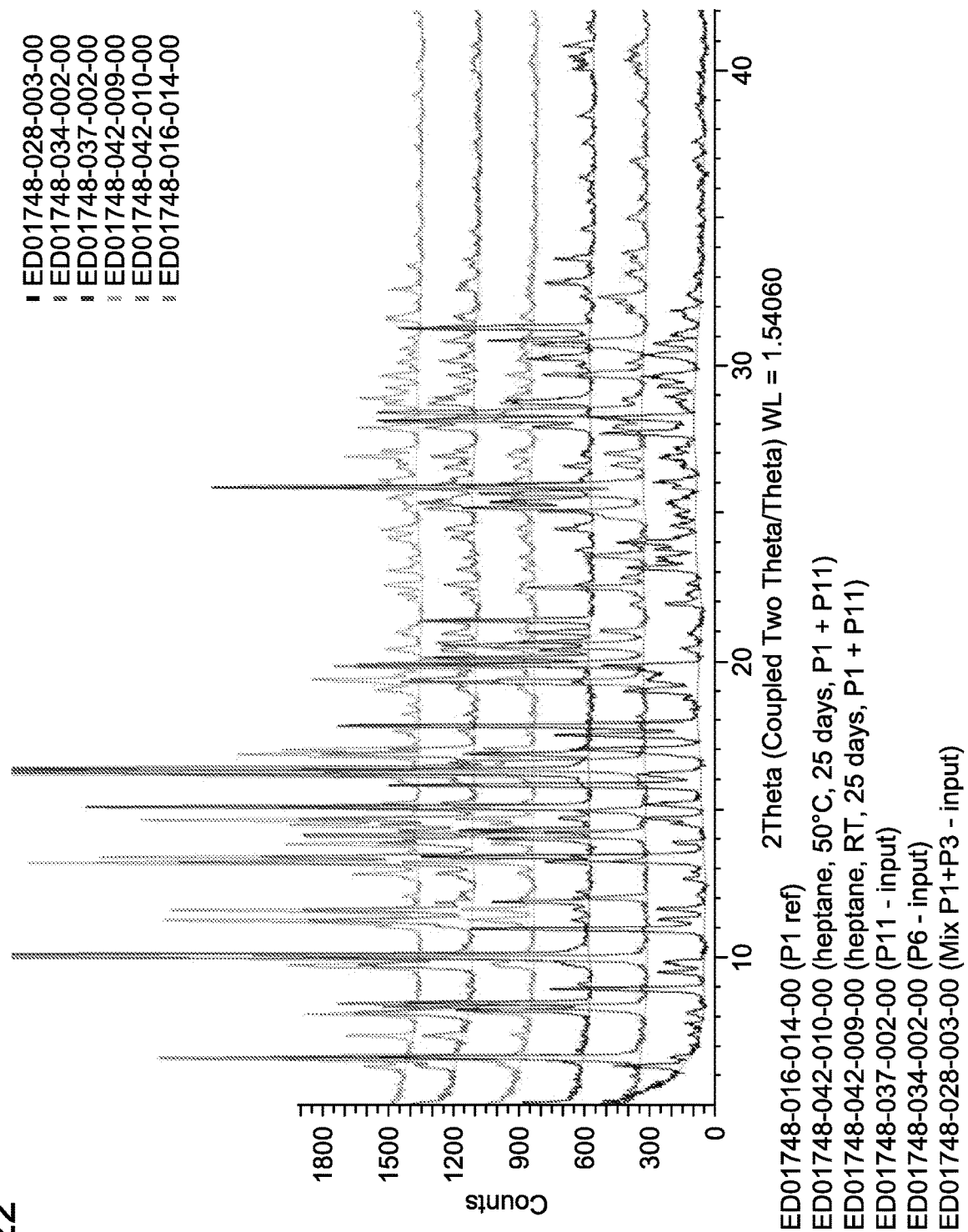

At room temperature and 50° C., after 1 day, all of the competitive slurries of the mixture of Pattern 1, Pattern 3, Pattern 6 and Pattern 11 materials in DIPE were converted to a Pattern 1 material. That is, it was confirmed that Pattern 1 is more thermodynamically stable than Pattern 3, Pattern 6 and Pattern 11 in DIPE at room temperature and 50° C. under the experimental conditions. In heptane, the mixture of Pattern 1 and Pattern 11 was present at room temperature and 50° C. after standing for 25 days, but no Pattern 6 remained. From this result, it was confirmed that Pattern 1 is more thermodynamically stable than Pattern 11 and Pattern 6 (FIGS. 21 and 22).

In the above, the present invention was described with reference to examples. It will be understood by those of ordinary skill in the art that the present invention can be implemented in modified forms without departing from the essential features of the present invention. Therefore, the disclosed embodiments should be considered in a descriptive sense, rather than a limiting sense. The scope of the present invention is shown in the claims rather than the foregoing description, and all differences within the equivalent range thereto will be construed as being included in the present invention.

The invention claimed is:

1. A crystalline form of (1-(2-chlorophenyl)-(S)-1-hydroxypropyl-(S)-2-carbamate having peaks of Formula I

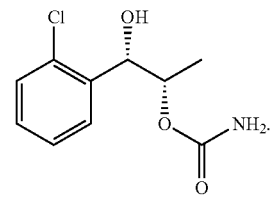

of a X-ray powder diffraction pattern at a diffraction angle (2θ) of 6.662°, 7.392°, 8.153°, 9.801°, 11.303°, 11.660°, 12.068°, 12.874°, 13.280°, 13.435°, 13.913°, 14.703°, 15.256°, 16.243°, 16.948°, 17.796°, 18.266°, 18.572°, 19.895°, 19.091°, 19.419°, 20.443°, 21.124°, 22.076°, 22.354°, 22.673°, 23.174°, 23.582°, 24.202°, 24.619°, 25.260°, 25.435°, 25.932°, 26.138°, 26.614°, 26.983°, 27.965°, 28.256°, 28.805°, 28.998°, 29.319°, 29.690°, 30.247°, 30.483°, 31.697°, 32.668° and 33.414°.

2. The crystalline form of claim 1, which has an endothermic peak at 89 to 90° C. in measurement by differential scanning calorimetry (DSC).

3. A method of preparing the crystalline form of (1-(2-chlorophenyl)-(S)-1-hydroxypropyl-(S)-2-carbamate of claim 1, the method comprising:
    forming an amorphous form by treating (1-(2-chlorophenyl)-(S)-1-hydroxypropyl-(S)-2-carbamate with one or more solvents selected from the group consisting of 1,4-dioxane, t-butanol, dichloromethane, water, and a mixed solvent thereof and
    removing the one or more solvents by rapid cooling, freeze drying or vacuum after (1-(2-chlorophenyl)-(S)-1-hydroxypropyl-(S)-2-carbamate is dissolved in the one or more solvents; and
    treating the resulting amorphous form with a solvent or a mixed solvent thereof, selected from the group consisting of acetone, methanol (MeOH), tetrahydrofuran, diisopropyl ether, ethanol (EtOH), methyl ethyl ketone, acetonitrile, 2-propanol, tert-butanol, 1,2-dimethoxyethane (DME), 1-propanol, 2-butanol, water, 1,4-dioxane, 2-methyl-1-propanol, 2-methoxyethanol, butyl acetate, methyl butyl ketone, 3-methyl-1-butanol, 1-pentanol, and cumene, and isolating the crystalline form of (1-(2-chlorophenyl)-(S)-1-hydroxypropyl-(S)-2-carbamate of claim 1.

4. A pharmaceutical composition comprising the crystalline form of (1-(2-chlorophenyl)-(S)-1-hydroxypropyl-(S)-2-carbamate of claim 1.

5. A method of treating a disease selected from the group consisting of muscle relaxation, movement disorder, spasticity, spasms, epilepsy, epilepsy-related syndrome, central nervous system disorders, Lou Gehrig's disease, multiple sclerosis, chronic pain, anxiety disorder, seizures, autism, depression, bipolar disorder, senile dementia or Alzheimer's and stroke, the method comprising administering the composition of claim 4.

\* \* \* \* \*

UNITED STATES PATENT AND TRADEMARK OFFICE
CERTIFICATE OF CORRECTION

| | | |
|---|---|---|
| PATENT NO. | : 11,795,139 B2 | Page 1 of 1 |
| APPLICATION NO. | : 17/837929 | |
| DATED | : October 24, 2023 | |
| INVENTOR(S) | : Yong Moon Choi | |

It is certified that error appears in the above-identified patent and that said Letters Patent is hereby corrected as shown below:

In the Claims

In Claim 1, Column 14, Lines 13-26, please replace:
"1. A crystalline form of (1-(2-chlorophenyl)-(S)-1-hydroxypropyl-(S)-2-carbamate having peaks of Formula I

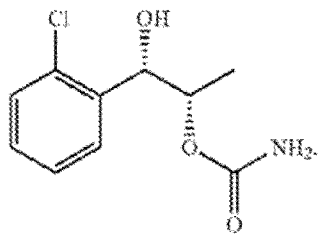

of a X-ray powder diffraction pattern at a diffraction angle"
With:
--1. A crystalline form of (1-(2-chlorophenyl)-(S)-1-hydroxypropyl-(S)-2-carbamate of Formula I

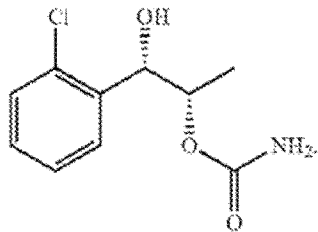

having peaks of a X-ray powder diffraction pattern at a diffraction angle--.

Signed and Sealed this
Twenty-third Day of April, 2024

*Katherine Kelly Vidal*

Katherine Kelly Vidal
*Director of the United States Patent and Trademark Office*